United States Patent
Mkademi et al.

(10) Patent No.: US 11,032,987 B2
(45) Date of Patent: Jun. 15, 2021

(54) ***BEGONIA* HYBRID 'GREEN LEAF WHITE 1605-01T1'**

(71) Applicant: Ernst Benary Samenzucht GmbH, Hann. Münden (DE)

(72) Inventors: Iris Mkademi, Hann. Münden (DE); Johannes Nebelmeir, Hann. Münden (DE)

(73) Assignee: Ernst Benary Samenzucht GmbH, Hann. Münden (DE)

( * ) Notice: Subject to any disclaimer, the term of this patent is extended or adjusted under 35 U.S.C. 154(b) by 0 days.

(21) Appl. No.: 16/670,674

(22) Filed: Oct. 31, 2019

(65) Prior Publication Data

US 2021/0127613 A1    May 6, 2021

(51) Int. Cl.
*A01H 6/18*     (2018.01)
*A01H 5/02*     (2018.01)

(52) U.S. Cl.
CPC ............... *A01H 6/185* (2018.05); *A01H 5/02* (2013.01)

(58) Field of Classification Search
CPC ..................................................... A01H 6/185
USPC ........................................................ Plt./345
See application file for complete search history.

(56) References Cited

U.S. PATENT DOCUMENTS

| | | |
|---|---|---|
| 5,777,196 A | 7/1998 | Hall |
| 5,948,957 A | 9/1999 | Chapko et al. |
| 5,959,185 A | 9/1999 | Streit et al. |
| 5,969,212 A | 10/1999 | Getschman |
| 5,973,234 A | 10/1999 | Mueller et al. |
| 5,977,445 A | 11/1999 | Soper et al. |
| PP17,575 P2 | 4/2007 | Heins |
| PP18,788 P3 | 5/2008 | Heins |
| PP19,401 P2 | 11/2008 | Heins |
| PP19,644 P2 | 1/2009 | Heins |
| PP19,653 P2 | 1/2009 | Heins |
| PP20,583 P2 | 12/2009 | Mehring-Lemper |
| PP20,586 P2 | 12/2009 | Mehring-Lemper |
| 9,295,208 B2 | 3/2016 | Kratzenberg |
| 9,295,209 B2 | 3/2016 | Kratzenberg |
| 9,949,453 B1 * | 4/2018 | Kratzenberg .......... A01H 6/185 |
| 9,949,454 B1 | 4/2018 | Kratzenberg |
| 9,955,637 B1 | 5/2018 | Kratzenberg |
| 2019/0307089 A1 | 10/2019 | Kratzenberg |

* cited by examiner

*Primary Examiner* — David H Kruse
(74) *Attorney, Agent, or Firm* — Morrison & Foerster LLP

(57) ABSTRACT

A hybrid *Begonia* designated 'Green Leaf White 1605-01T1' is disclosed. The invention relates to the plants and parts thereof of hybrid *Begonia* 'Green Leaf White 1605-01T1', and to methods for producing other *Begonia* lines, cultivars or hybrids derived from the hybrid *Begonia* 'Green Leaf White 1605-01T1'.

13 Claims, 40 Drawing Sheets
(40 of 40 Drawing Sheet(s) Filed in Color)

BEGONIA HYBRID 'GREEN LEAF WHITE 1605-01T1'

FIELD OF THE INVENTION

The present invention relates to the field of plant breeding. In particular, the present invention relates to a new and distinctive *Begonia* interspecific hybrid designated 'Green Leaf White 1605-01T1'.

BACKGROUND OF THE INVENTION

*Begonia* is a genus of perennial flowering plants that is native to moist subtropical and tropical climates and contains more than 1,600 species and hundreds of hybrids. Depending on the climate, some *Begonia* plants are grown indoors as ornamental houseplants or are cultivated outside for their bright colorful flowers. *Begonia* plants have fleshy leaves and stems, and the leaves are often magnificently colored and textured. Cultivated *Begonia* plants often have showy flowers of white, pink, scarlet or yellow color.

*Begonia* plants are monoecious, with unisexual male and female flowers occurring separately on the same plant; the male contains numerous stamens and the female has a large inferior ovary and two to four branched or twisted stigmas. In most *Begonia* species, the fruit is a winged capsule containing numerous minute seeds. The leaves, which are often large and variously marked or variegated, are usually asymmetric.

The American *Begonia* Society classifies begonias into eight major groups including: cane-like, shrub, rhizomatous, semperflorens (wax type), tuberous, rex, trailing-scandent, and thick stemmed. The *Begonia* genus is unusual in that species throughout the genus, even those from different continents, can frequently be hybridized with each other, which has led to an enormous number of cultivars. Most begonias propagate easily by seed or from stem cuttings.

*Begonia* plants are a popular and valuable ornamental plant. Thus, there is a continued need to develop new *Begonia* hybrids with unique colors, robust outdoor performance, large size, and unique habit shape.

SUMMARY OF THE INVENTION

In order to meet these needs, the present invention is directed to improved *Begonia* hybrids. In one embodiment, the present invention is directed to *Begonia* hybrid seed designated as 'Green Leaf White 1605-01T1' having ATCC Accession Number PTA-126675. In one embodiment, the present invention is directed to a *Begonia* hybrid plant and plant parts isolated therefrom produced by growing 'Green Leaf White 1605-01T1' *Begonia* seed. In another embodiment, the present invention is directed to a *Begonia* hybrid plant and plant parts isolated therefrom having all the physiological and morphological characteristics of a *Begonia* hybrid plant produced by growing 'Green Leaf White 1605-01T1' *Begonia* seed having ATCC Accession Number PTA-126675.

*Begonia* plant parts include *Begonia* flowers, leaves, ovules, pollen, seeds, fruits, parts of fruits, cells, portions thereof, and the like. In another embodiment, the present invention is further directed to *Begonia* flowers, leaves, ovules, pollen, cells, and/or portions thereof isolated from 'Green Leaf White 1605-01T1' *Begonia* plants. In certain embodiments, the present invention is further directed to pollen or ovules isolated from 'Green Leaf White 1605-01T1' *Begonia* plants. In another embodiment, the present invention is further directed to protoplasts produced from 'Green Leaf White 1605-01T1' *Begonia* plants. In another embodiment, the present invention is further directed to tissue culture of 'Green Leaf White 1605-01T1' *Begonia* plants, and to *Begonia* plants regenerated from the tissue culture, where the plant has all of the morphological and physiological characteristics of a *Begonia* hybrid plant produced by growing 'Green Leaf White 1605-01T1' *Begonia* seed having ATCC Accession Number PTA-126675. In certain embodiments, tissue culture of 'Green Leaf White 1605-01T1' *Begonia* plants produced from protoplasts or cells from a plant part selected from flower, leaf, anther, pistil, stem, petiole, root, root tip, fruit, seed, cotyledon, hypocotyl, embryo, and meristematic cell.

In yet another embodiment, the present invention is further directed to a method of selecting *Begonia* plants, by a) growing 'Green Leaf White 1605-01T1' *Begonia* plants where the 'Green Leaf White 1605-01T1' plants are grown from *Begonia* seed having ATCC Accession Number PTA-126675 and b) selecting a plant from step a). In another embodiment, the present invention is further directed to *Begonia* plants, plant parts and seeds produced by the *Begonia* plants where the *Begonia* plants are isolated by the selection method of the invention.

According to the invention, there is provided a hybrid *Begonia* plant designated 'Green Leaf White 1605-01T1'. This invention thus relates to the plants of *Begonia* 'Green Leaf White 1605-01T1', to the plant parts of *Begonia* 'Green Leaf White 1605-01T1' and to methods for producing a *Begonia* plant containing in its genetic material one or more transgenes and to the transgenic *Begonia* plants produced by that method. This invention also relates to methods for producing other *Begonia* cultivars or hybrids derived from *Begonia* hybrid 'Green Leaf White 1605-01T1' and to the *Begonia* cultivars and hybrids derived by the use of those methods.

In another embodiment, the present invention is directed to single gene converted plants of *Begonia* hybrid 'Green Leaf White 1605-01T1'. The single transferred gene may preferably be a dominant or recessive allele. Preferably, the single transferred gene will confer such traits as sex determination, herbicide resistance or tolerance, insect resistance or tolerance, resistance or tolerance for bacterial, fungal, or viral disease, improved flower color, improved flower quality and/or quantity, stress tolerance and/or resistance, physical appearance, prolificacy, improved plant color, improved plant size, improved habit size and shape, improved leaf size and shape, improved seasonal performance, improved branching, improved flowering, and the like. The single gene may be a naturally occurring *Begonia* gene or a transgene introduced through genetic engineering techniques.

In another embodiment, the present invention is directed to methods for developing *Begonia* plants in a *Begonia* plant breeding program using plant breeding techniques including recurrent selection, backcrossing, pedigree breeding, restriction fragment length polymorphism enhanced selection, genetic marker enhanced selection and transformation. Marker loci such as restriction fragment polymorphisms or random amplified DNA have been published for many years and may be used for selection (See, Pierce et al., *HortScience* (1990) 25:605-615; Wehner, T., *Cucurbit Genetics Cooperative Report*, (1997) 20: 66-88; and Kennard et al., *Theorical Applied Genetics* (1994) 89:217-224). Seeds, *Begonia* plants, and parts thereof produced by such breeding methods are also part of the invention.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 4A shows a top view of a plant of *Begonia* hybrid 'Green Leaf White 1605-01T1', showing branches without older leaves. FIG. 4B shows a top view of a plant of *Begonia* hybrid 'Green Leaf White 1605-01T1', showing branches only with flower leaves. FIG. 4C shows branches of *Begonia* hybrid 'Green Leaf White 1605-01T1' (1605-01T1).

FIG. 5A shows a plant and flowers of *Begonia* hybrid 'Green Leaf White 1605-01T1' ("1605-01T1", on right) and *Begonia* variety Tophat™ White (on left), showing branches without older leaves. FIG. 5B shows plants of *Begonia* hybrid 'Green Leaf White 1605-01T1' ("1605-01T1", on right) and *Begonia* variety Tophat™ White (on left). FIG. 5C shows a top view of a plant of *Begonia* variety Tophat™ White, showing branches without older leaves. FIG. 5D shows a top view of a plant of *Begonia* variety Tophat™ White, showing branches only with flower leaves. FIG. 5E shows a side view of plants of *Begonia* hybrid 'Green Leaf White 1605-01T1' ("1605-01T1", in center), *Begonia* variety Tophat™ White (on left), and *Begonia* hybrid BIG® Green Leaf Red (on right), showing branches with only flower leaves. FIG. 5F shows branches of *Begonia* hybrid 'Green Leaf White 1605-01T1' ("White Green Leaf", on right) and *Begonia* variety Tophat™ White (on left). FIG. 5G shows branches of *Begonia* variety Tophat™ White. FIG. 5H shows branches of *Begonia* hybrid BIG® Green Leaf Red.

FIG. 6A shows a first germination scan of *Begonia* hybrid 'Green Leaf White 1605-01T1'. FIG. 6B shows a second germination scan of *Begonia* hybrid 'Green Leaf White 1605-01T1'.

FIG. 7A shows a first germination scan of *Begonia* variety Tophat™ White. FIG. 7B shows a second germination scan of *Begonia* variety Tophat™ White. FIG. 7C shows a first germination scan of *Begonia* hybrid BIG® Green Leaf Red. FIG. 7D shows a second germination scan of *Begonia* hybrid BIG® Green Leaf Red.

FIG. 8A shows a top view of a sowing tray of *Begonia* hybrid Green Leaf White 1605-01T1'. FIG. 8B shows a side view of a young plant of *Begonia* hybrid 'Green Leaf White 1605-01T1' ("Big Exp White Green Leaf"). FIG. 8C shows a top view of a young plant of *Begonia* hybrid 'Green Leaf White 1605-01T1' ("Big Exp White Green Leaf").

FIG. 9A shows a top view of a sowing tray of *Begonia* variety Tophat™ White ("TopHat White"). FIG. 9B shows a side view of a young plant of *Begonia* variety Tophat™ White ("TopHat White"). FIG. 9C shows a top view of a young plant of *Begonia* variety Tophat™ White ("TopHat White"). FIG. 9D shows a top view of a sowing tray of *Begonia* hybrid BIG® Green Leaf Red ("BIG Red Green Leaf"). FIG. 9E shows a side view of a young plant of *Begonia* hybrid BIG® Green Leaf Red ("BIG Red Green Leaf"). FIG. 9F shows a top view of a young plant of *Begonia* hybrid BIG® Green Leaf Red ("BIG Red Green Leaf").

FIG. 10A shows a top view of a plant of *Begonia* hybrid 'Green Leaf White 1605-01T1' ("Big Exp White Green Leaf"). FIG. 10B shows a side view of a plant of *Begonia* hybrid 'Green Leaf White 1605-01T1' ("Big Exp White Green Leaf"). FIG. 10C shows a top view of a plant and flowers of *Begonia* hybrid 'Green Leaf White 1605-01T1' ("Big Exp White Green Leaf"). FIG. 10D shows a side view of a plant and flower of *Begonia* hybrid 'Green Leaf White 1605-01T1'. FIG. 10E shows a top view of a plant and flowers of *Begonia* hybrid 'Green Leaf White 1605-01T1'. FIG. 10F shows a side view of a plant and flowers of *Begonia* hybrid 'Green Leaf White 1605-01T1'. FIG. 10G shows a top view of a plant and flowers of *Begonia* hybrid 'Green Leaf White 1605-01T1' ("Big Exp White Green Leaf"). FIG. 10H shows a side view of a plant and flowers of *Begonia* hybrid 'Green Leaf White 1605-01T1'.

FIG. 11A shows a top view of a plant of *Begonia* variety Tophat™ White. FIG. 11P shows a side view of a plant and flowers of *Begonia* hybrid BIG® Green Leaf Red.

FIG. 12A shows the mean number of branches (y-axis) for different *Begonia* varieties (x-axis). The total sum of all counted branches was used as a proxy of total number of branches. FIG. 12B shows the total number of second order branches (y-axis) for different *Begonia* varieties (x-axis). FIG. 12C shows the mean length of second order branches (y-axis) for different *Begonia* varieties (x-axis). FIG. 12D shows the mean number of third order branches (y-axis) for different *Begonia* varieties (x-axis). FIG. 12E shows the mean height of 10 tallest branches (y-axis) for different *Begonia* varieties (x-axis). In FIGS. 12A-12E, from right to left along the x-axis, the variety BIG® Red Bronze Leaf is shown in teal, BIG® Deluxxe Red Bronze Leaf is shown in orange, BIG® Deluxxe Red Green Leaf is shown in purple, BIG® Red Green Leaf is shown in pink, 'Green Leaf White 1605-01T1' is shown in green, Megawatt™ Red Green Leaf is shown in goldenrod, Tophat™ White is shown in brown, Viking Red Green Leaf is shown in gray, and Viking XL Red Green Leaf is shown in white.

DETAILED DESCRIPTION OF THE INVENTION

Figure 1:
FIG. 1 shows a mature plant and flowers of *Begonia* hybrid 'Green Leaf White 1605-01T1'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher seed yield, improved flower color, resistance to diseases and insects, tolerance to drought and heat, and better agronomic quality.

Definitions

In the description and tables that follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Cell. Cell as used herein includes a plant cell, whether isolated, in tissue culture or incorporated in a plant or plant part.

Cotyledon. One of the first leaves of the embryo of a seed plant; typically one or more in monocotyledons, two in dicotyledons, and two or more in gymnosperms.

Essentially all the physiological and morphological characteristics. A plant having essentially all the physiological and morphological characteristics means a plant having the physiological and morphological characteristics of the recurrent parent, except for the characteristics derived from the converted gene.

F#. The "F" symbol denotes the filial generation, and the # is the generation number, such as $F_1$, $F_2$, $F_3$, etc.

Gene. As used herein, "gene" refers to a segment of nucleic acid. A gene can be introduced into a genome of a species, whether from a different species or from the same species, using transformation or various breeding methods.

Genetically Modified. Describes an organism that has received genetic material from another, or had its genetic material modified, resulting in a change in one or more of its phenotypic characteristics. Methods used to modify, introduce or delete the genetic material may include mutation breeding, backcross conversion, genetic transformation, single and multiple gene conversion, and/or direct gene transfer.

Genotype. Refers to the genetic constitution of a cell or organism.

Internode. An "internode" refers to the stem segment between nodes.

Length/Width (L/W) Ratio. This ratio is determined by dividing the average length (L) by the average width (W).

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, herbicide tolerance, insect resistance, disease resistance, waxy starch, modified fatty acid metabolism, modified phytic acid metabolism, modified carbohydrate metabolism, modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Multiple Gene Converted (Conversion). Multiple gene converted (conversion) includes plants developed by a plant breeding technique called backcrossing wherein essentially all of the desired morphological and physiological characteristics of an inbred are recovered, while retaining two or more genes transferred into the inbred via crossing and backcrossing. The term can also refer to the introduction of multiple genes through genetic engineering techniques known in the art.

Plant. As used herein, the term "plant" includes reference to an immature or mature whole plant, including a plant from which seed or grain or anthers have been removed. Seed or embryo that will produce the plant is also considered to be the plant.

Plant Height. Plant height in centimeters is taken from soil surface to the tip at harvest.

Plant Parts. As used herein, the term "plant parts" (or a part thereof) includes but is not limited to protoplasts, leaves, stems, roots, root tips, anthers, pistils, seed, embryo, pollen, ovules, cotyledon, hypocotyl, pod, flower, shoot, tissue, petiole, cells, meristematic cells, fruit, portions thereof, and the like.

Pubescence. This refers to a covering of very fine hairs closely arranged on the leaves, stems and glumes of the plant.

Quantitative Trait Loci (QTL). As used herein, "quantitative trait loci" refers to genetic loci that control to some degree numerically representable traits that are usually continuously distributed.

Regeneration. As used herein, "regeneration" refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Rogueing. Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Single gene converted. Single gene converted or conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

Overview of the *Begonia* Hybrid Variety 'Green Leaf White 1605-01T1'

Figure 2:
FIG. 2 shows a side view of a plant and flowers of *Begonia* hybrid 'Green Leaf White 1605-01T1'.
Figure 3:
FIG. 3 shows a top view of a plant and flowers of *Begonia* hybrid 'Green Leaf White 1605-01T1'.
Figure 4A:
FIGS. 4A-4C show plants and branches of *Begonia* hybrid 'Green Leaf White 1605-01T1'.
Figure 4B:
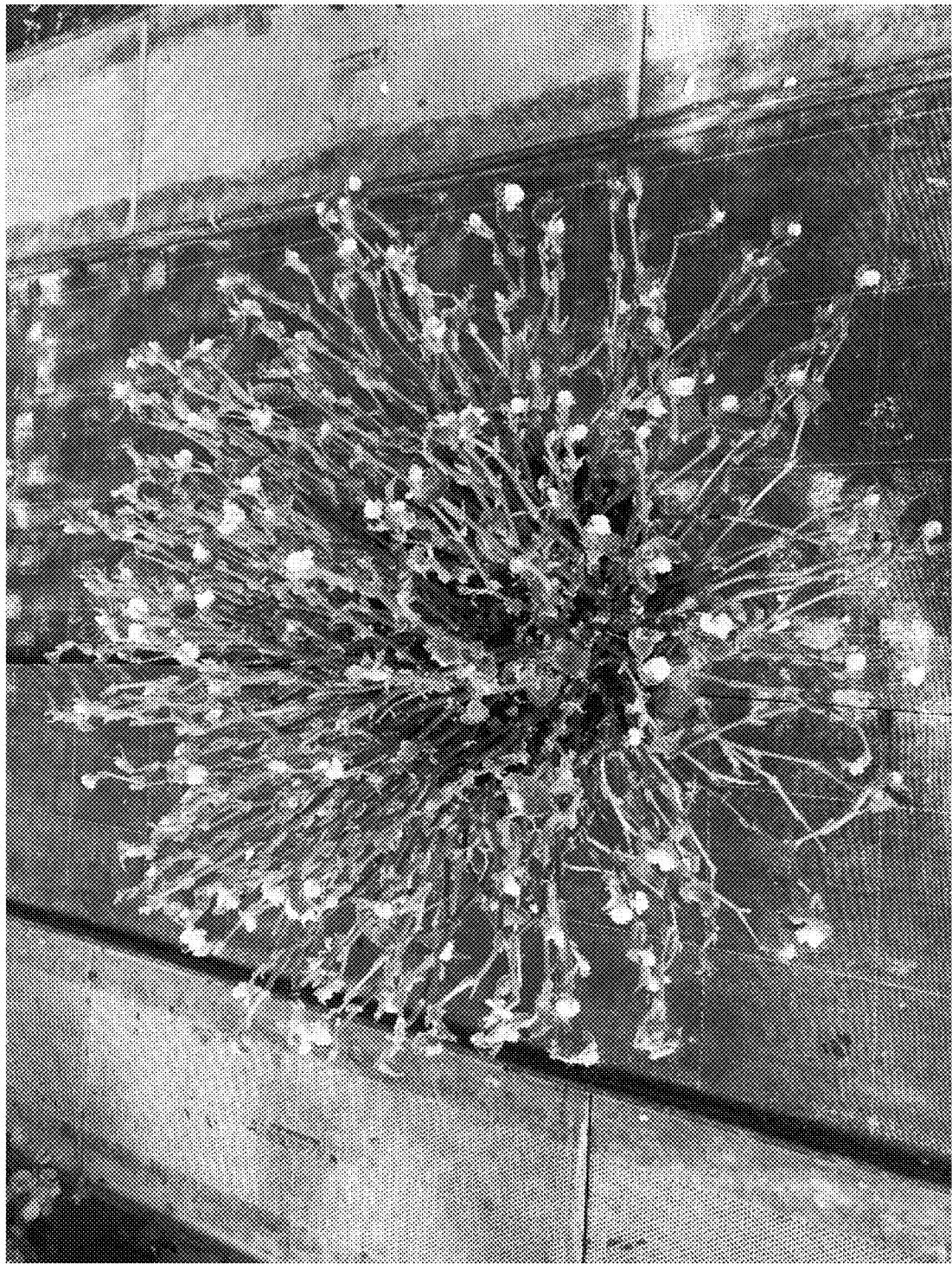
Figure 4C:
Figure 5A:
FIGS. 5A-5H show comparisons between *Begonia* hybrid 'Green Leaf White 1605-01T1' (1605-01T1) and the *Begonia* varieties Tophat™ White, and BIG® Green Leaf Red.
Figure 5B:
Figure 5C:
Figure 5D:
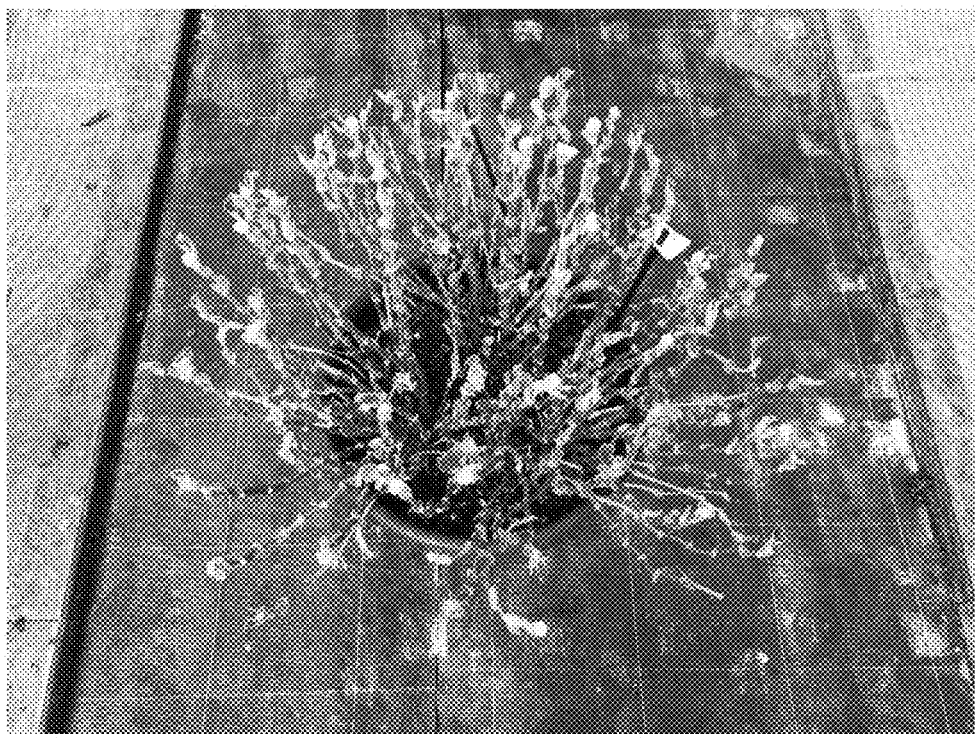
Figure 5E:
Figure 5F:
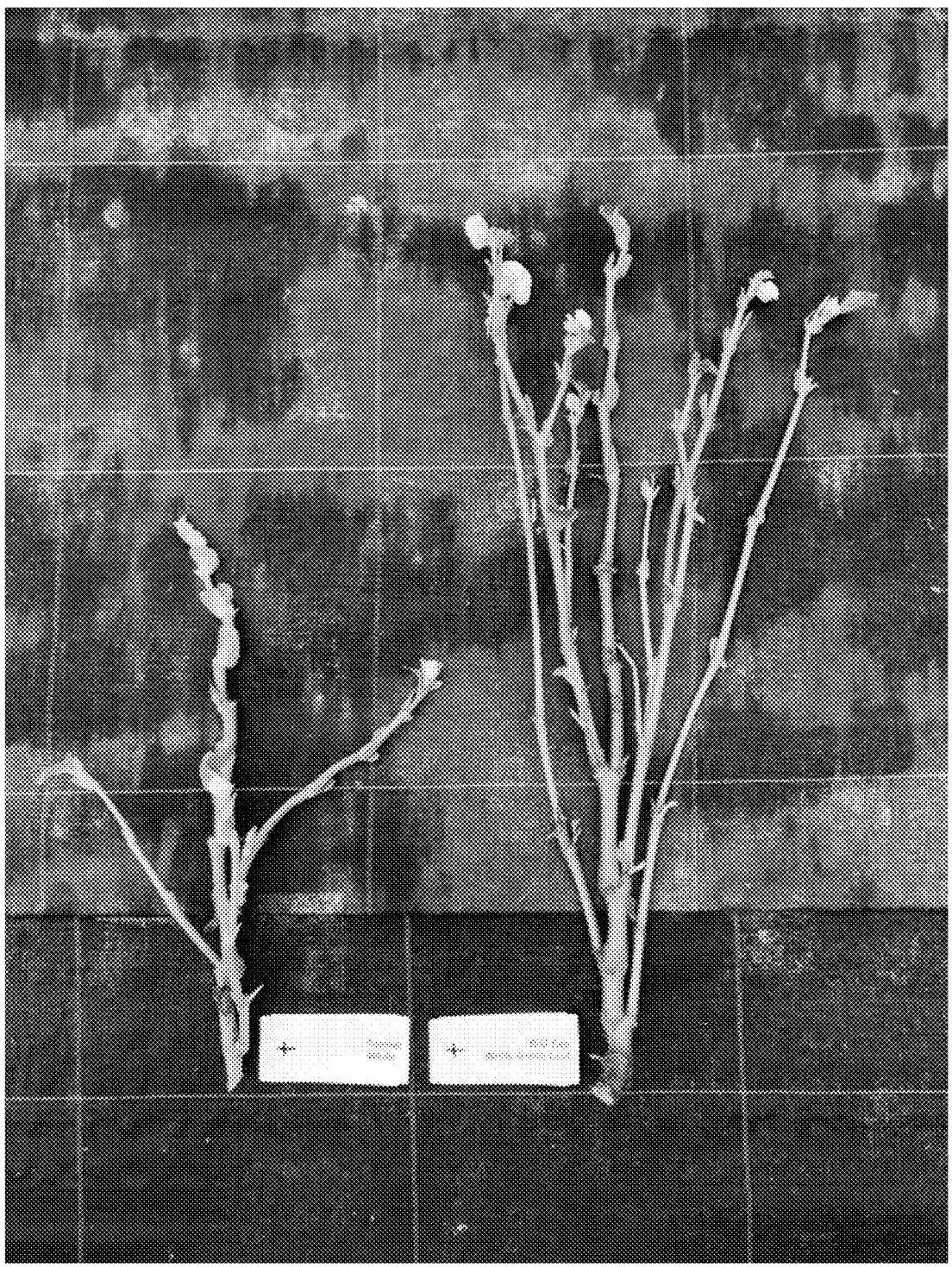
Figure 5G:
Figure 5H:
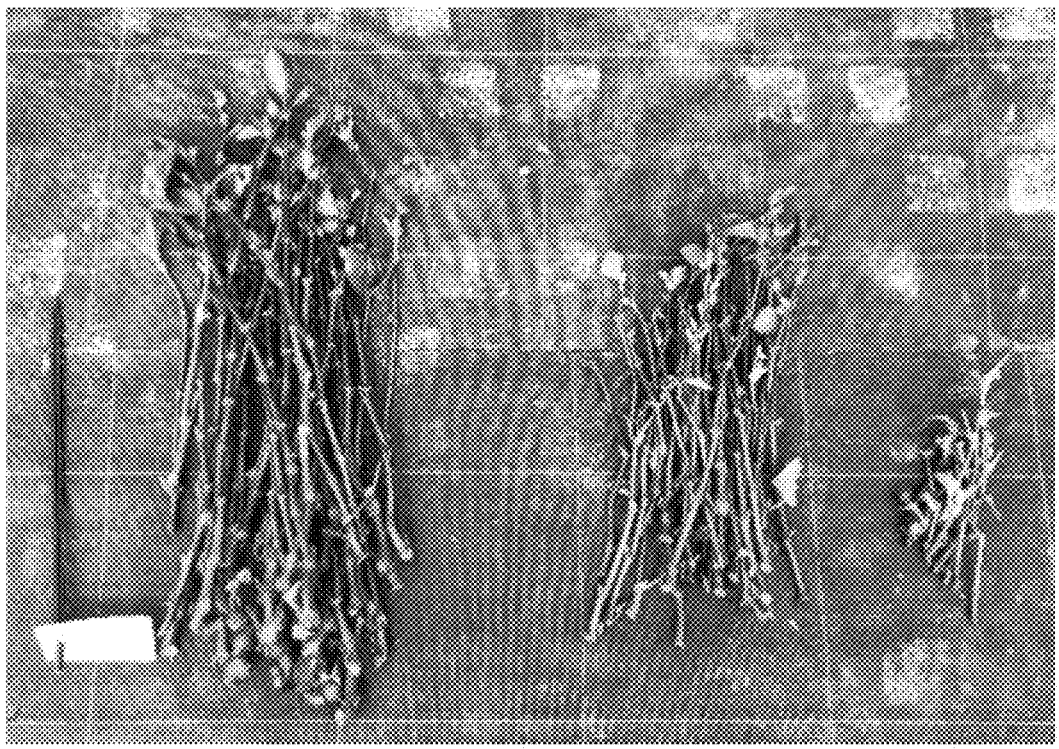
Figure 6A:
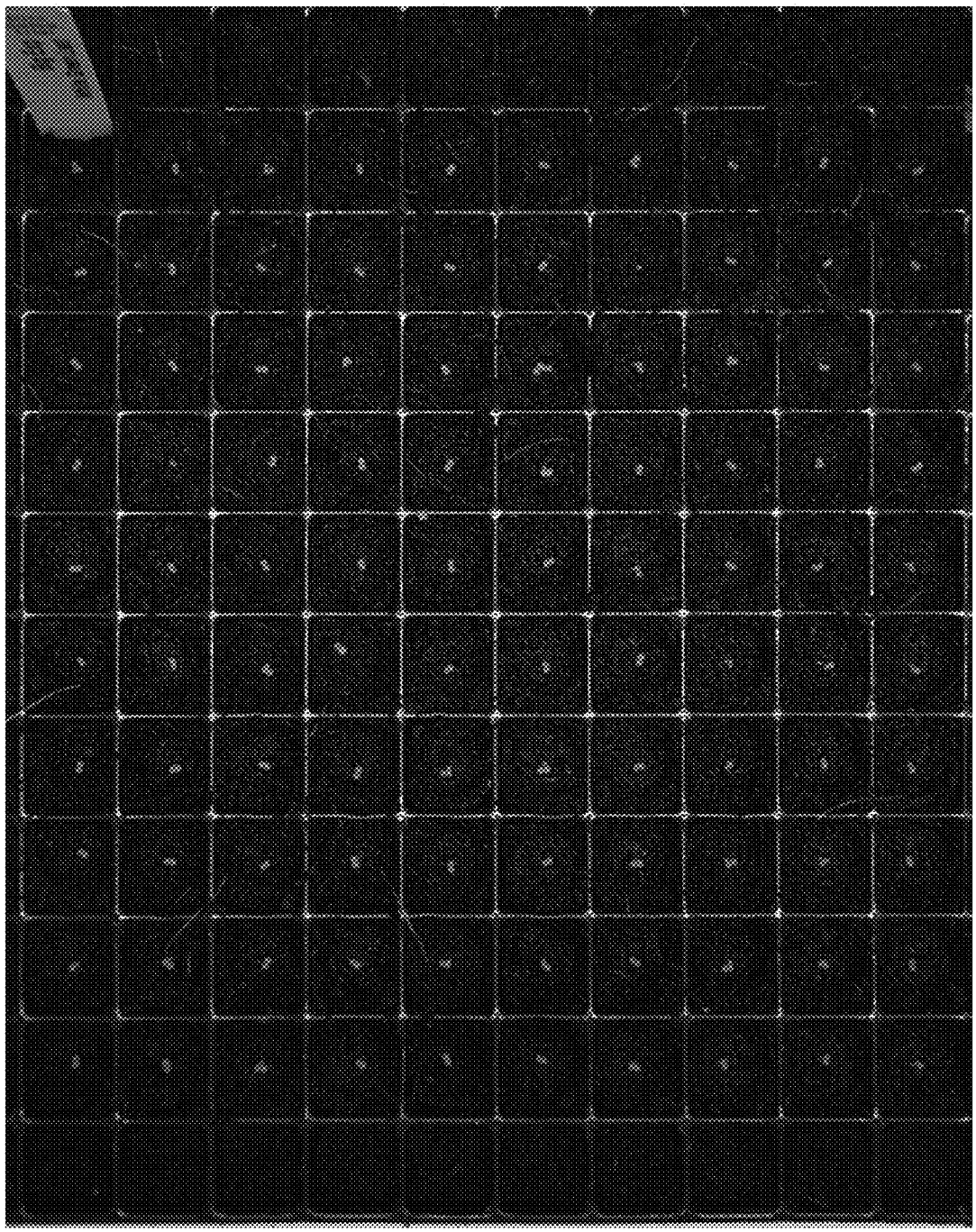
FIGS. 6A-6B show germination scans of *Begonia* hybrid 'Green Leaf White 1605-01T1'.
Figure 6B:
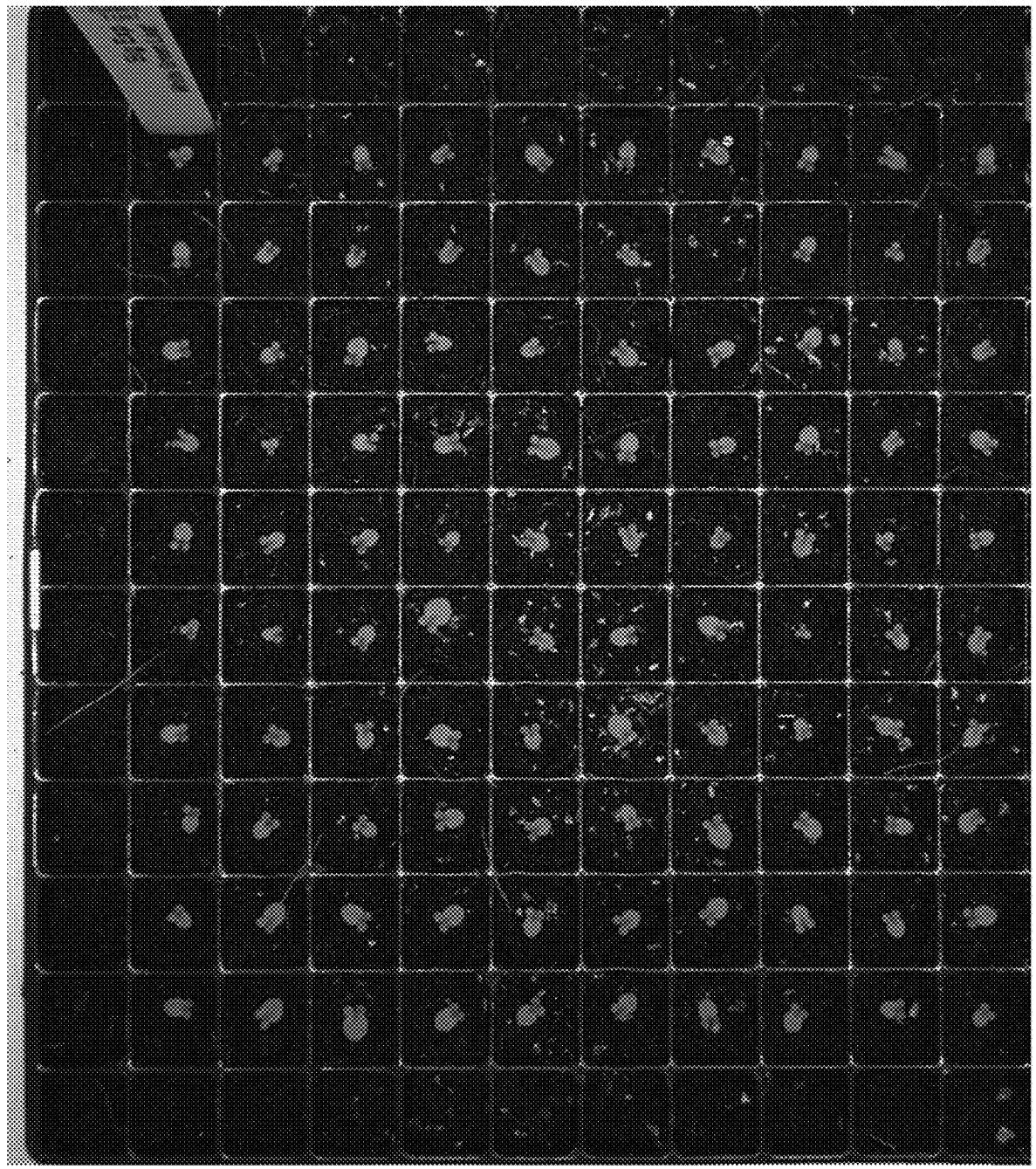
Figure 7B:
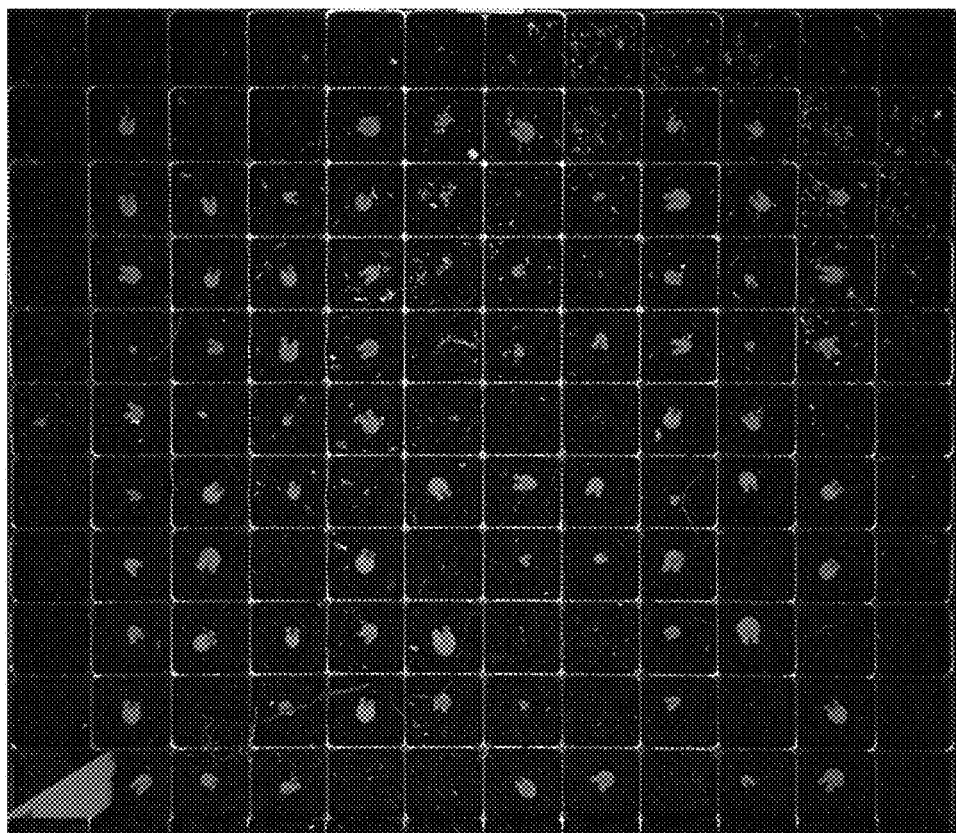
FIGS. 7A-7D show germination scans of *Begonia* varieties Tophat™ White and BIG® Green Leaf Red.
Figure 7A:
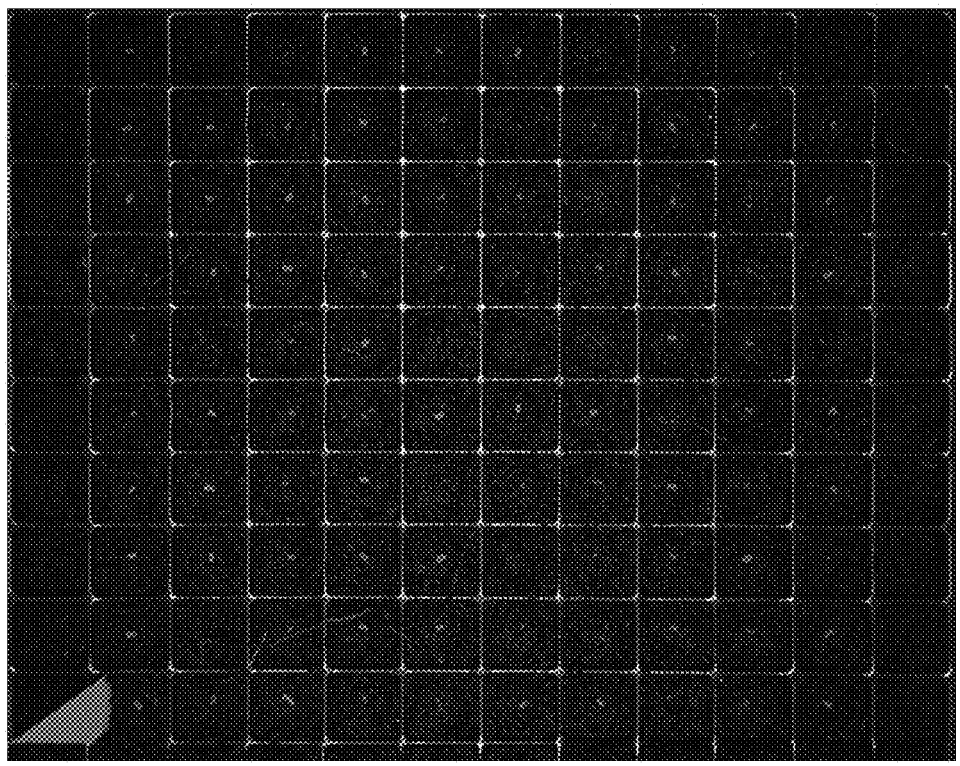
Figure 7D:
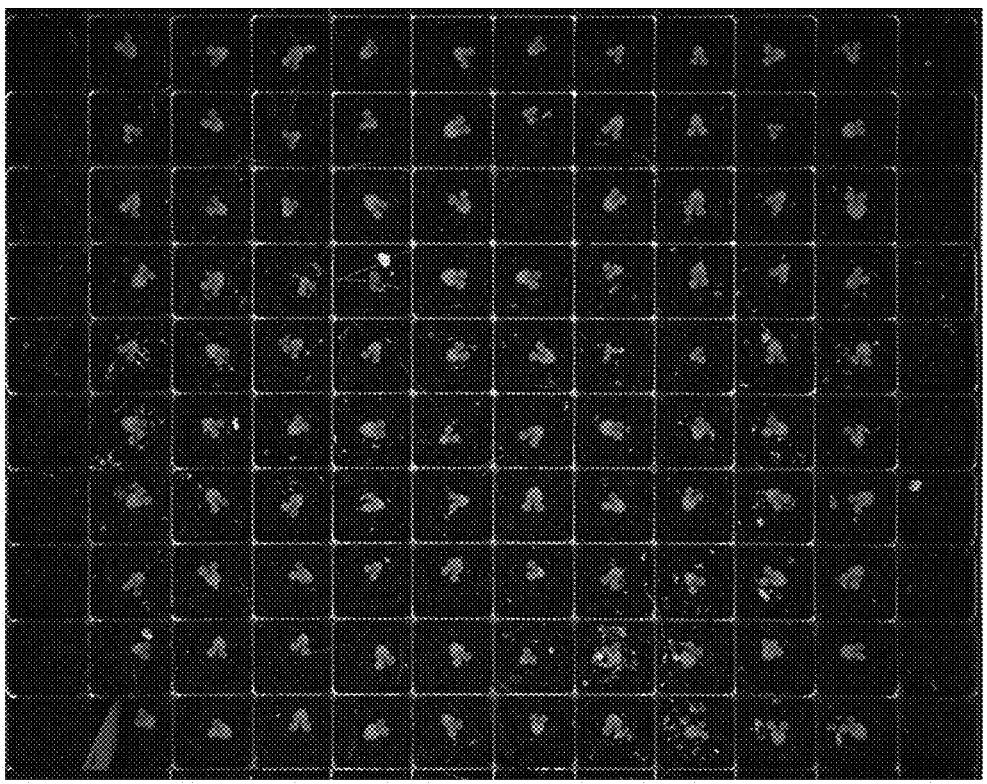
Figure 7C:
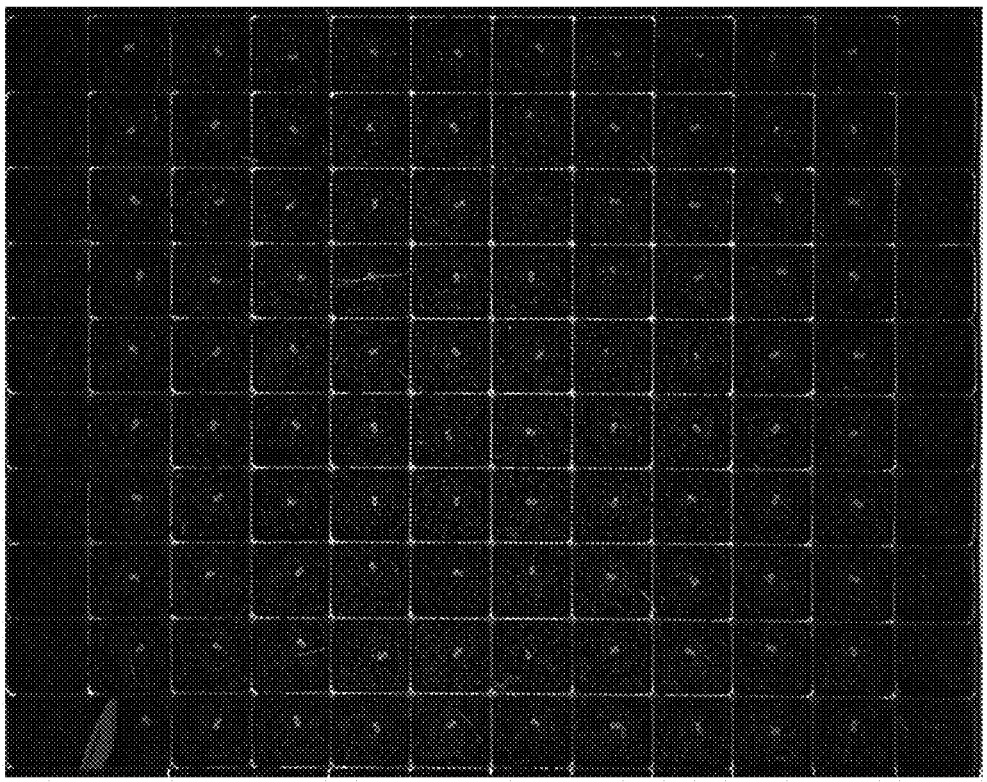
Figure 8A:
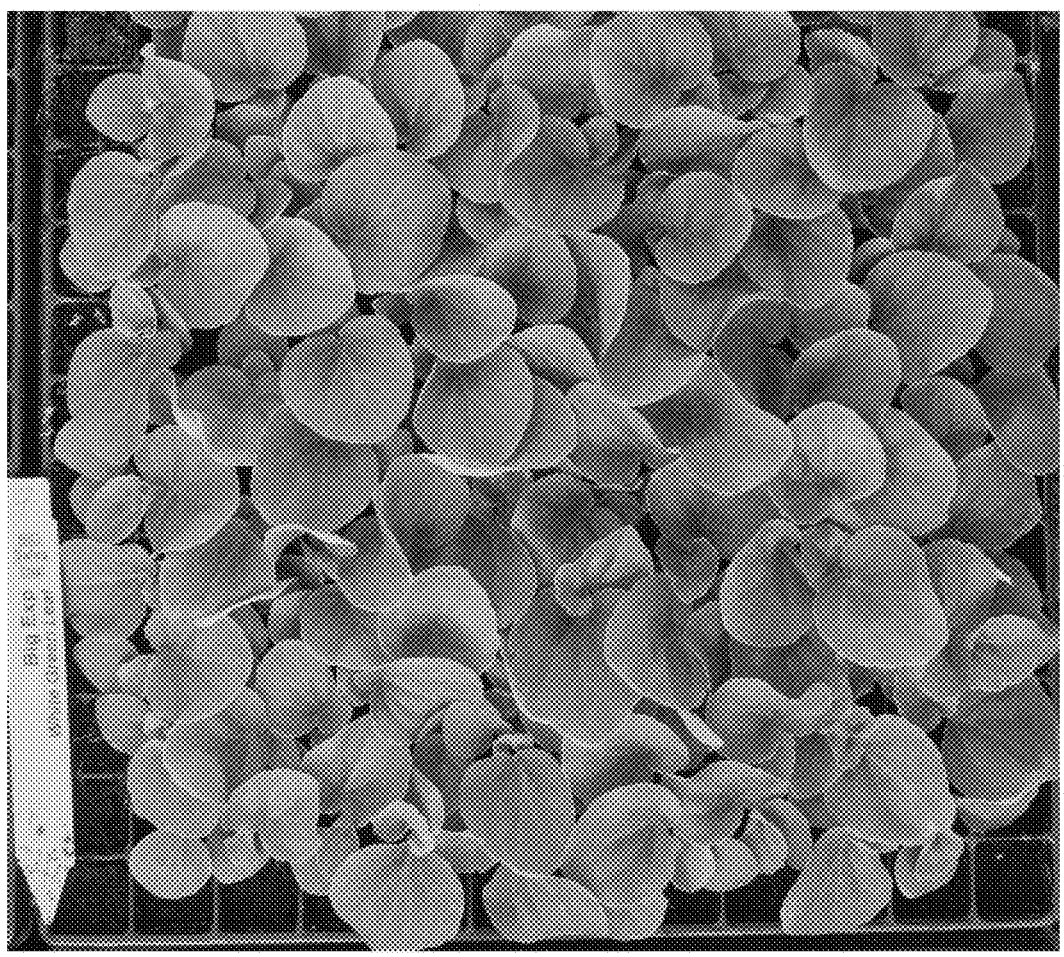
FIGS. 8A-8C show sowing trays and young plants of *Begonia* hybrid 'Green Leaf White 1605-01T1' ("Big Exp White Green Leaf").
Figure 8B:
Figure 8C:
Figure 9B:
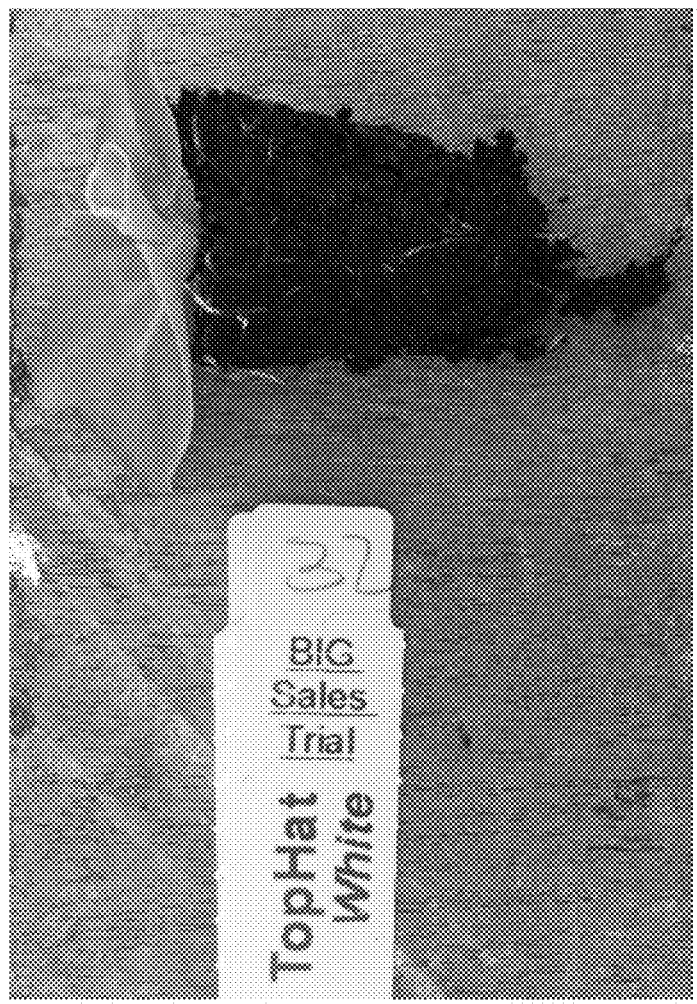
FIGS. 9A-9F show sowing trays and young plants of *Begonia* variety Tophat™ White and *Begonia* hybrid BIG® Green Leaf Red.
Figure 9A:
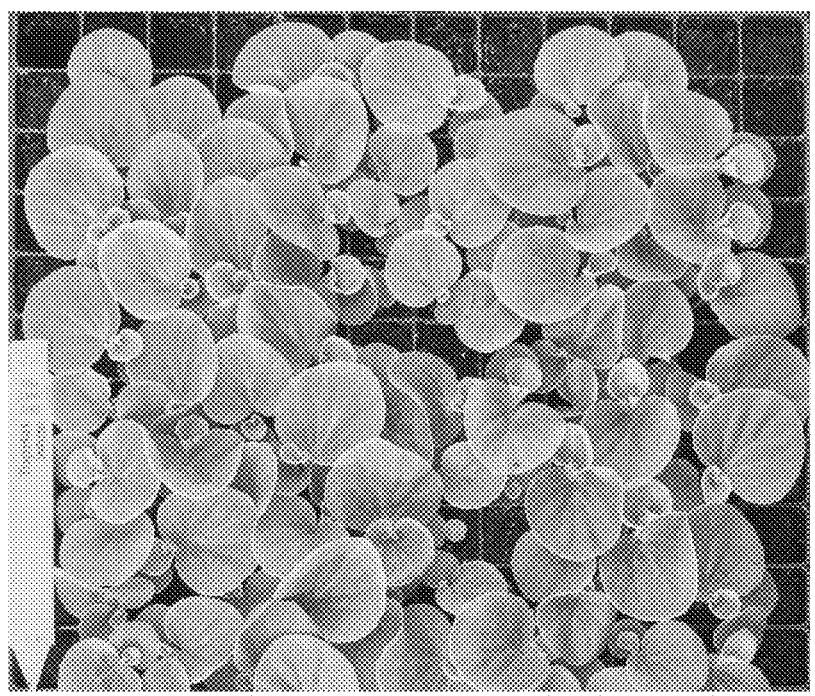
Figure 9D:
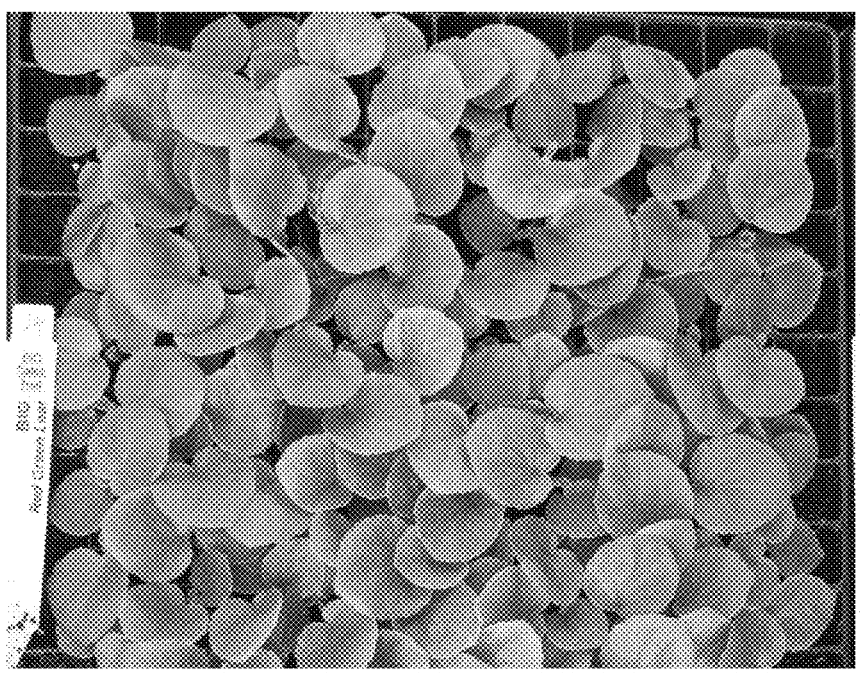
Figure 9C:
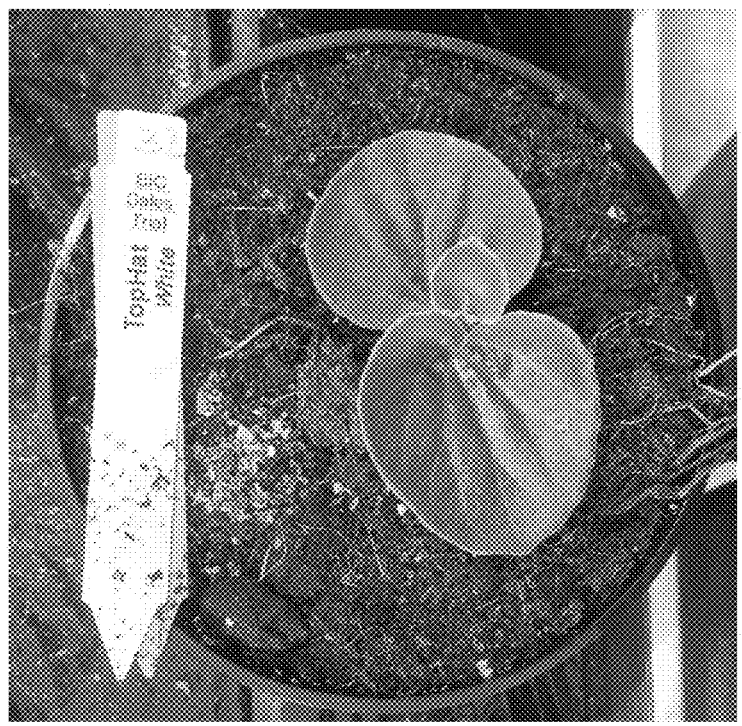
Figure 9F:
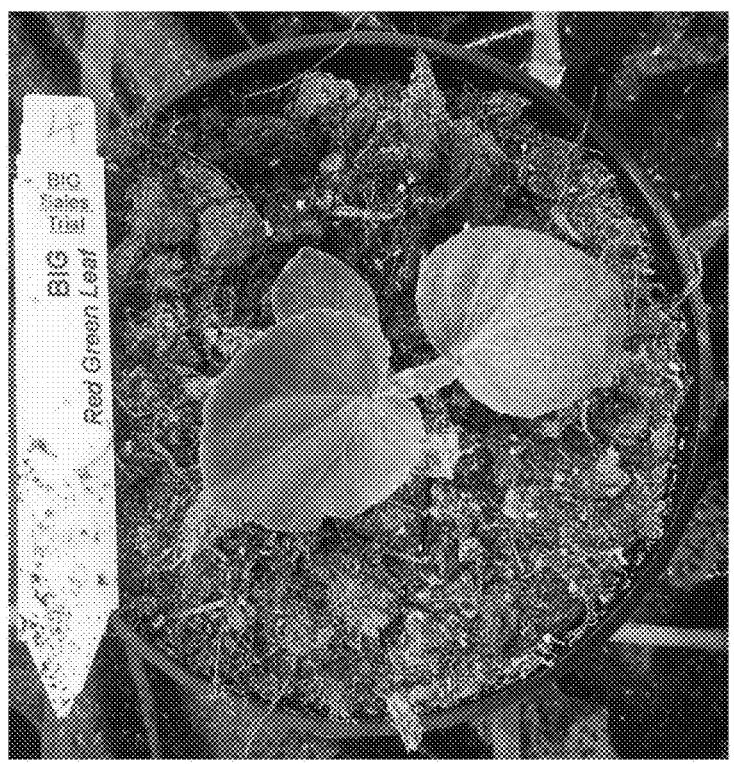
Figure 9E:
Figure 10A:
FIGS. 10A-10H show plants and flowers of *Begonia* hybrid 'Green Leaf White 1605-01T1'.
Figure 10B:
Figure 10C:
Figure 10D:
Figure 10E:
Figure 10F:
Figure 10G:
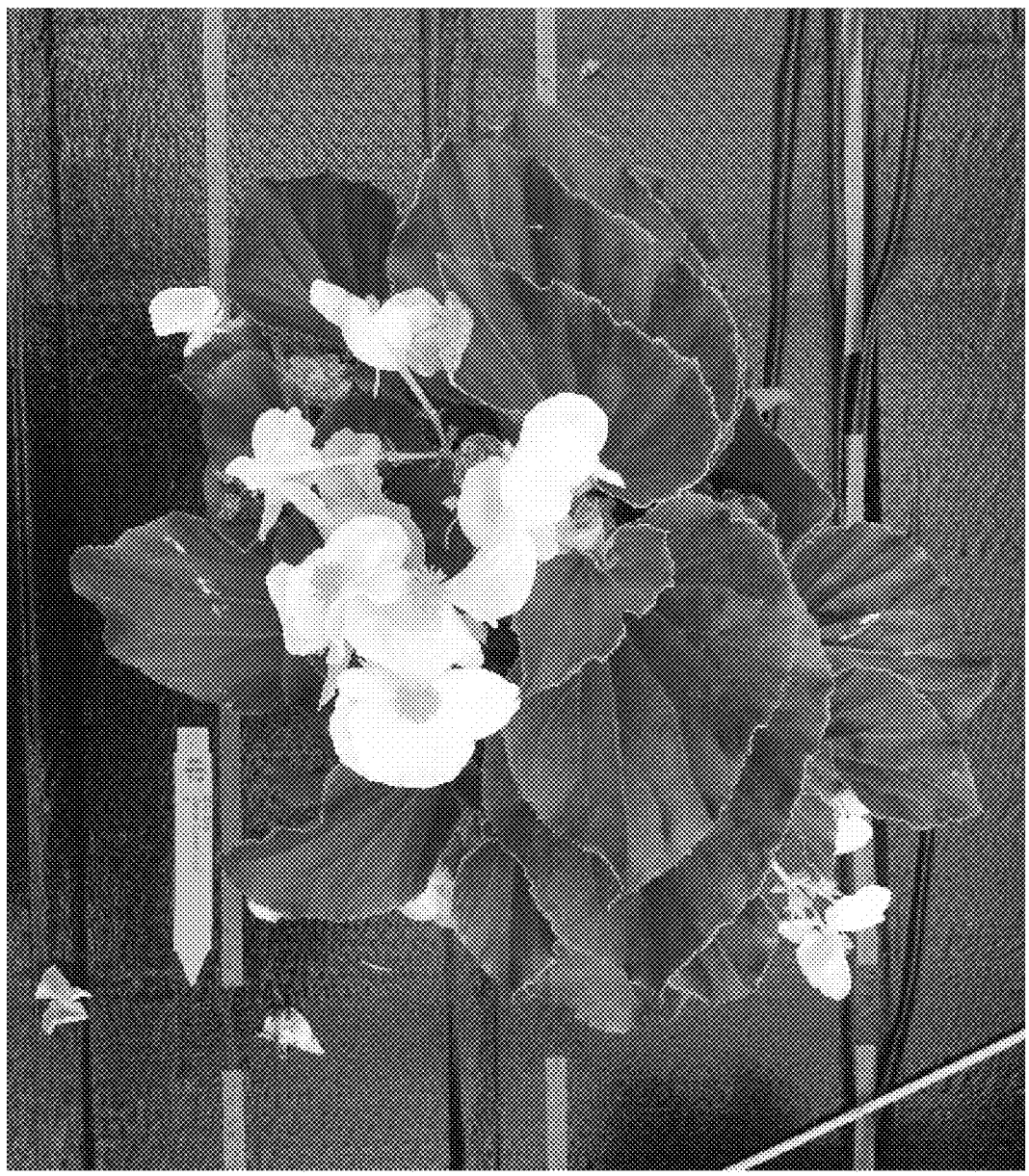
Figure 10H:
Figure 11A:
FIGS. 11A-11P show plants of *Begonia* variety Tophat™ White and *Begonia* hybrid BIG® Green Leaf Red.
Figure 11B:
FIG. 11B shows a side view of a plant of *Begonia* variety Tophat™ White.
Figure 11C:
FIG. 11C shows a top view of a plant and flowers of *Begonia* variety Tophat™ White.
Figure 11D:
FIG. 11D shows a side view of a plant and flowers of *Begonia* variety Tophat™ White.
Figure 11E:
FIG. 11E shows a top view of a plant and flowers of *Begonia* variety Tophat™ White.
Figure 11F:
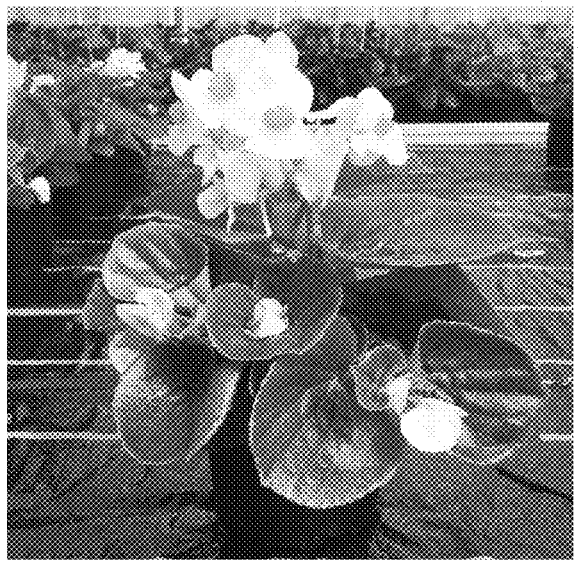
FIG. 11F shows a side view of a plant and flowers of *Begonia* variety Tophat™ White.
Figure 11G:
FIG. 11G shows a top view of a plant and flowers of *Begonia* variety Tophat™ White.
Figure 11H:
FIG. 11H shows a side view of a plant and flowers of *Begonia* variety Tophat™ White.
Figure 11I:
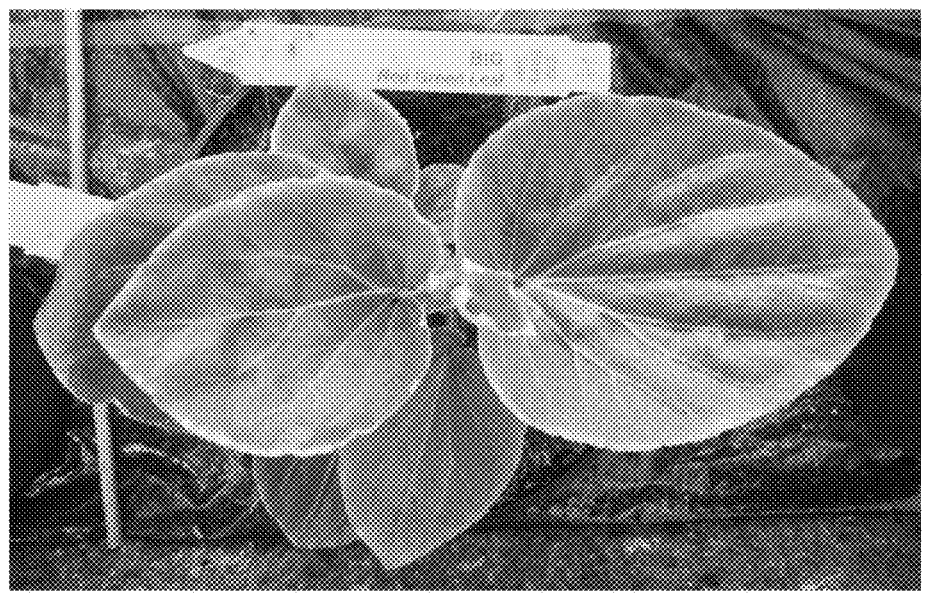
FIG. 11I shows a top view of a plant of *Begonia* hybrid BIG® Green Leaf Red.
Figure 11J:
FIG. 11J shows a side view of a plant of *Begonia* hybrid BIG® Green Leaf Red.
Figure 11K:
FIG. 11K shows a top view of a plant and flowers of *Begonia* hybrid BIG® Green Leaf Red.
Figure 11L:
FIG. 11L shows a side view of a plant and flowers of *Begonia* hybrid BIG® Green Leaf Red.
Figure 11M:
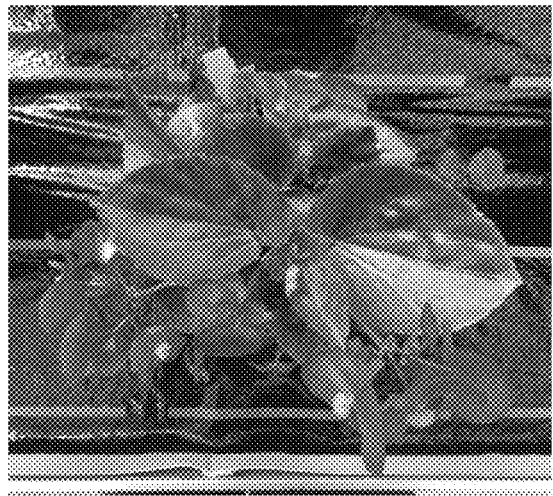
FIG. 11M shows a top view of a plant and flowers of *Begonia* hybrid BIG® Green Leaf Red.
Figure 11N:
FIG. 11N shows a side view of a plant and flowers of *Begonia* hybrid BIG® Green Leaf Red.
Figure 11O:
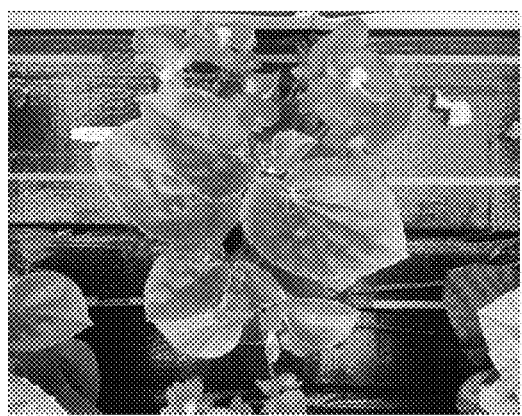
FIG. 11O shows a top view of a plant and flowers of *Begonia* hybrid BIG® Green Leaf Red.
Figure 11P:

*Begonia* hybrid 'Green Leaf White 1605-01T1' is a unique interspecific hybrid having a rounded and closed habit, large green leaves, white flowers, a high number of branches, long branches in the second order, and a large size. *Begonia* hybrid 'Green Leaf White 1605-01T1' has an upright and rounded growth habit, a high number of branches, an increased number of leaves, and uniquely shaped leaves. *Begonia* hybrid 'Green Leaf White 1605-01T1' has a growing season that includes spring and summer until first frost, and is suitable for growing in all regions where bedding plants are used. *Begonia* hybrid 'Green Leaf White 1605-01T1' also has an extraordinary outdoor performance and flowers in both full sun and in shade, though it flowers better in the shade. Additionally, *Begonia* hybrid 'Green Leaf White 1605-01T1' is an outstanding late season performer. FIG. 1 depicts a mature plant and flowers of *Begonia* hybrid 'Green Leaf White 1605-01T1'. FIG. 2 depicts a side view of a plant and flowers of *Begonia* hybrid 'Green Leaf White 1605-01T1'. FIG. 3 depicts a top view of a plant and flowers of *Begonia* hybrid 'Green Leaf White 1605-01T1'. FIGS. 4A-4C depict plants and branches of *Begonia* hybrid 'Green Leaf White 1605-01T1'. FIGS. 6A-6B depict germination scans of *Begonia* hybrid 'Green Leaf White 1605-01T1'. FIGS. 8A-8C depict sowing trays and young plants of *Begonia* hybrid 'Green Leaf White 1605-01T1'. FIGS. 10A-10H depict plants and flowers of *Begonia* hybrid 'Green Leaf White 1605-01T1'. *Begonia* hybrid 'Green Leaf White 1605-01T1' is the result of numerous generations of plant selections chosen for its size, branching, plant and flower color, habit shape, leaf shape, leaf size, and leaf density.

*Begonia* hybrid 'Green Leaf White 1605-01T1' reproduces true from seeds and has shown uniformity and stability for the traits, within the limits of environmental influence for the traits. *Begonia* hybrid 'Green Leaf White 1605-01T1' has been produced and tested a sufficient number of years with careful attention to uniformity of plant type. *Begonia* hybrid 'Green Leaf White 1605-01T1' has been produced with continued observation for uniformity of the parental lines.

Objective Description of Hybrid *Begonia* 'Green Leaf White 1605-01T1'

*Begonia* hybrid variety 'Green Leaf White 1605-01T1' has the following morphologic and other characteristics:

Classification:
 Family: Begoniaceae
 Botanical name: Interspecific hybrid of *Begonia semperflorens* and another *Begonia* species
 Common name: *Begonia*
Plant:
 Propagation type: Seeds
 Form: Annual
 Growth habit: Upright and rounded; covers a wide area and has curving branches that go lower than the rim of the pot
 Branching habit: Basal
 Height: 53 cm+
 Width: 45 cm+
 Time to initiate roots: During germination
 Root description: Fibrous
Lateral Branches:
 Length: 50 cm+
 Diameter at base: 1.0 cm
 Diameter at tip: 0.5 cm
 Angle: 30°
 Texture: None
 Color at base: RHS 177B
 Color at tip: RHS 145B
Leaves:
 Arrangement: Alternate
 Length: 12 cm to 13 cm
 Width: 10 cm to 11 cm
 Shape: Stalked, asymmetrical
 Apex: Pointed
 Base: Aliform
 Color of upper surface: RHS 147A
 Color of lower surface: RHS 147B
 Texture (both upper and lower surfaces): Slightly wavy, moderately shiny
 Venation pattern: Reticulated
 Venation color: RHS 144B
 Glossiness: Low
Petioles:
 Length: 3.0 cm to 3.5 cm
 Width: 0.6 cm to 0.7 cm
 Color of upper surface: RHS 146D
 Color of lower surface: RHS 146D
Flower Buds:
 Length: 2.2 cm to 2.5 cm
 Diameter: 2.5 cm to 2.7 cm
 Shape: Heart-shaped without apex
 Color: RHS 155B
Flower:
 Bloom habit: Dichasium
 Male flower form: Zygomorphic
 Female flower form: Cycle
 Color of upper surface: RHS 155B
 Color of lower surface: RHS 155B
 Fragrance: None
 Inflorescence height: 7 cm to 8 cm
 Inflorescence diameter: 11 cm to 12 cm
 Flower diameter of male flower: 4 cm to 5 cm
 Flower diameter of female flower: 3.7 cm to 3.8 cm
 Flower height of male flower: 6 cm
 Flower height of female flower: 4 cm to 4.2 cm
Pedicels:
 Length of male pedicel: 1.7 cm to 1.8 cm
 Length of female pedicel: 1 cm to 1.2 cm
 Diameter: 0.2 cm to 0.3 cm; top: 0.2 cm Angle: 35°

Texture: Smooth

Color: Male: RHS 143C; female: RHS 155D

Peduncles:

Length: 8.5 cm to 10 cm

Diameter at base: 0.4 cm

Diameter at tip: 0.2 cm

Angle: Variable

Texture: Smooth

Color: Green part: RHS 144C; brown part: RHS 166D

Reproductive Organs:

Stamens: Many

Filament color: RHS 13A

Amount of pollen: Sparse

Color of pollen: Non-pollen color

Pistil: Curled

Stigma number: 6

Mature style color: RHS 17A

Younger style color: RHS 14B

Disease and Insect Resistance: Nothing Specific

Comparisons to Most Similar Varieties

The performance of *Begonia* hybrid 'Green Leaf White 1605-01T1' has been evaluated in facilities for greenhouse and outdoor trials in Hannoversch Münden, Germany. *Begonia* hybrid 'Green Leaf White 1605-01T1' was tested in comparison to the *Begonia semperflorens* variety Tophat™ White as shown in Table 1.

TABLE 1

| Characteristic | 'Green Leaf White 1605-01T1' | Tophat ™ White |
| --- | --- | --- |
| Sterility | Completely sterile | Less sterile |
| Flower size | Slightly smaller flowers | Slightly larger flowers |
| Number of branches | Significantly more branches | Significantly fewer branches |
| Number of branches of second and third order | Significantly more branches of second and third order | Significantly fewer branches of second and third order |
| Length of branches of second order | Significantly longer branches in second order | Significantly shorter branches in second order |
| Height | Significantly higher | Significantly lower |

Figure 12A:
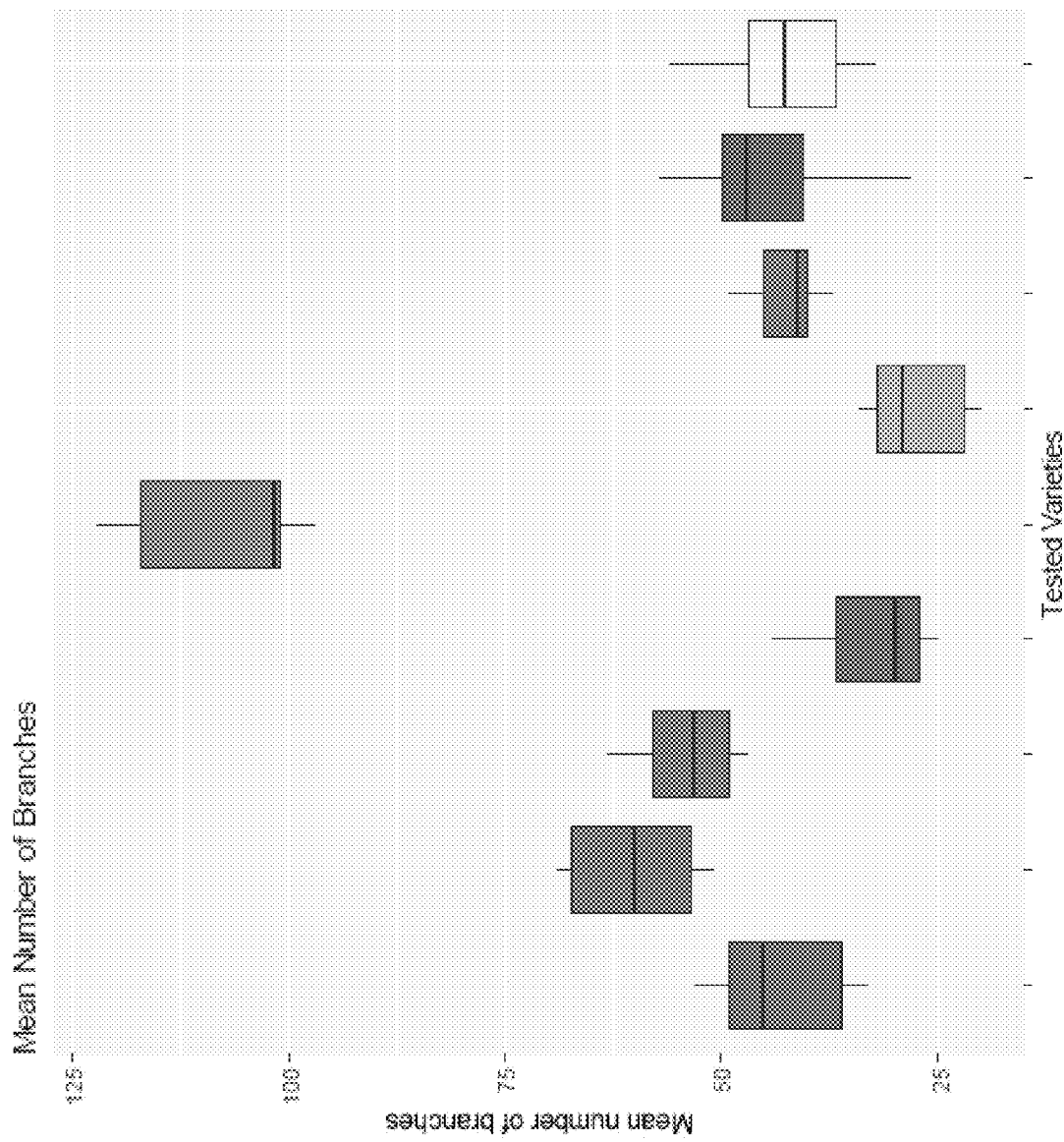
FIGS. 12A-12E show quantitative comparisons of *Begonia* hybrid 'Green Leaf White 1605-01T1' with other *Begonia* varieties.

Traits of *Begonia* hybrid 'Green Leaf White 1605-01T1' were quantified and statistically evaluated in comparison to other *Begonia* varieties. The total number of branches of hybrid 'Green Leaf White 1605-01T1' was determined, as shown in FIG. 12A and Table 2. As shown in Table 2, a Least Significant Difference (LSD) Test was performed to statistically compare the total number of branches of 'Green Leaf White 1605-01T1' to other *Begonia* varieties. In this and the following LSD tests, *Begonia* varieties with the same letter test group were not significantly different. 'Green Leaf White 1605-01T1' was placed in a distinct group by the LSD test, meaning that 'Green Leaf White 1605-01T1' had significantly more branches than any other tested *Begonia*. In addition, a one sample t-test was performed to compare the number of branches in 'Green Leaf White 1605-01T1' to the other tested *Begonia* varieties. The t-test showed that 'Green Leaf White 1605-01T1' had a mean total number of branches that was at least double the other tested begonias (p-value=0.003207).

TABLE 2

| Begonia variety | Total number of branches | LSD Test Group |
| --- | --- | --- |
| 'Green Leaf White 1605-01T1' | 107.50000 | a |
| BIG ® Deluxxe Red Bronze Leaf | 60.16667 | b |
| BIG ® Deluxxe Red Green Leaf | 53.83333 | bc |
| Viking Red Green Leaf | 44.66667 | cd |
| BIG ® Red Bronze Leaf | 43.20000 | cd |
| Viking XL Red Green Leaf | 42.66667 | cd |
| Tophat ™ White | 42.33333 | cd |
| BIG ® Red Green Leaf | 32.33333 | de |
| Megawatt ™ Red Green Leaf | 27.33333 | e |

Figure 12B:
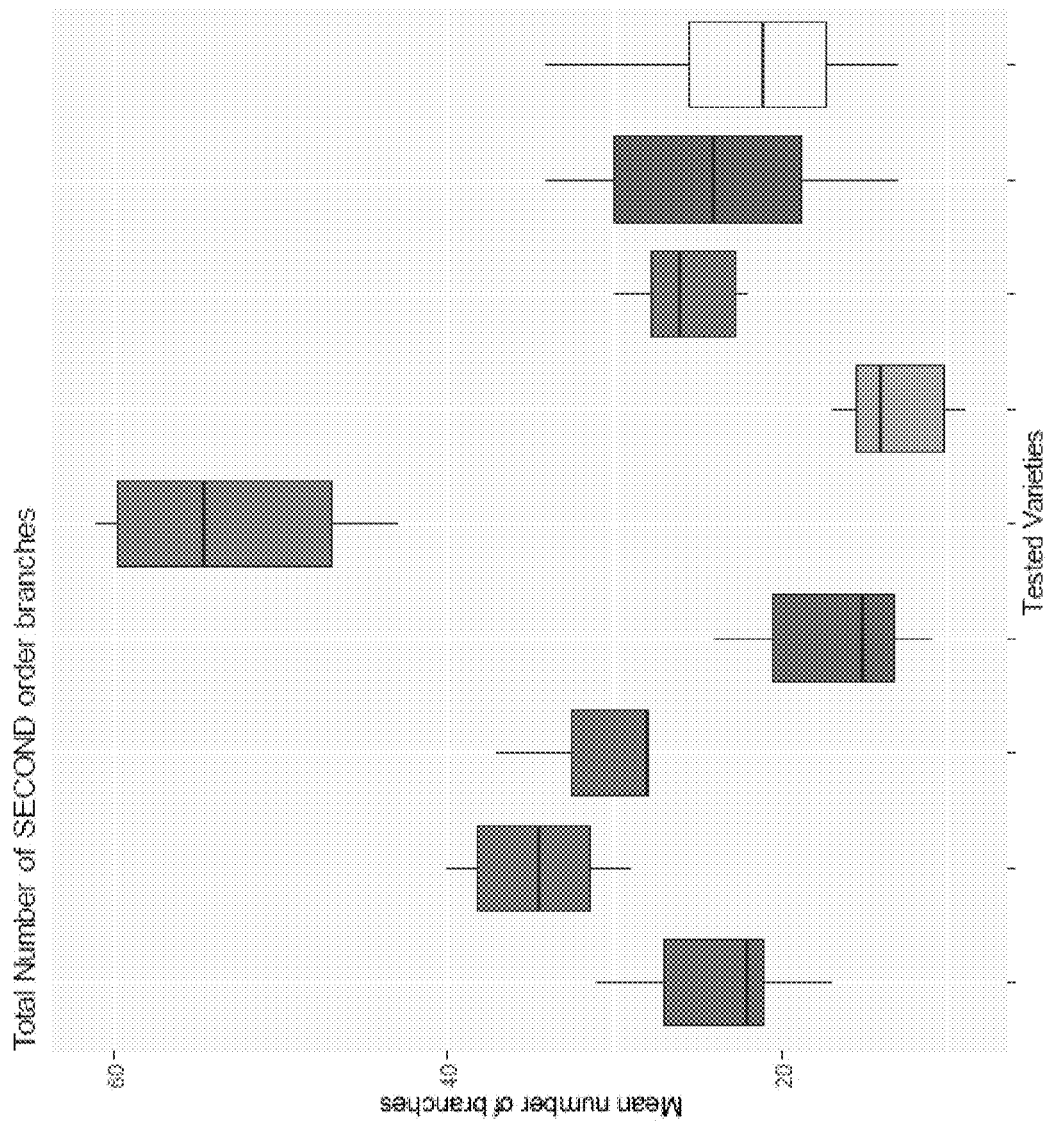

The number of second order branches of 'Green Leaf White 1605-01T1' compared to other *Begonia* varieties was quantified, as shown in FIG. 12B and Table 3. 'Green Leaf White 1605-01T1' was placed in a distinct group by a LSD test, meaning that 'Green Leaf White 1605-01T1' had significantly more second order branches than any other tested *Begonia*.

| Begonia variety | Total number of branches | LSD Test Group |
| --- | --- | --- |
| 'Green Leaf White 1605-01T1' | 53.16667 | a |
| BIG ® Deluxxe Red Bronze Leaf | 34.66667 | b |
| BIG ® Deluxxe Red Green Leaf | 30.50000 | bc |
| Tophat ™ White | 25.66667 | bcd |
| Viking Red Green Leaf | 24.00000 | cd |
| BIG ® Red Bronze Leaf | 23.60000 | cde |
| Viking XL Red Green Leaf | 22.00000 | cde |
| BIG ® Red Green Leaf | 16.66667 | de |
| Megawatt ™ Red Green Leaf | 13.16667 | e |

Figure 12C:
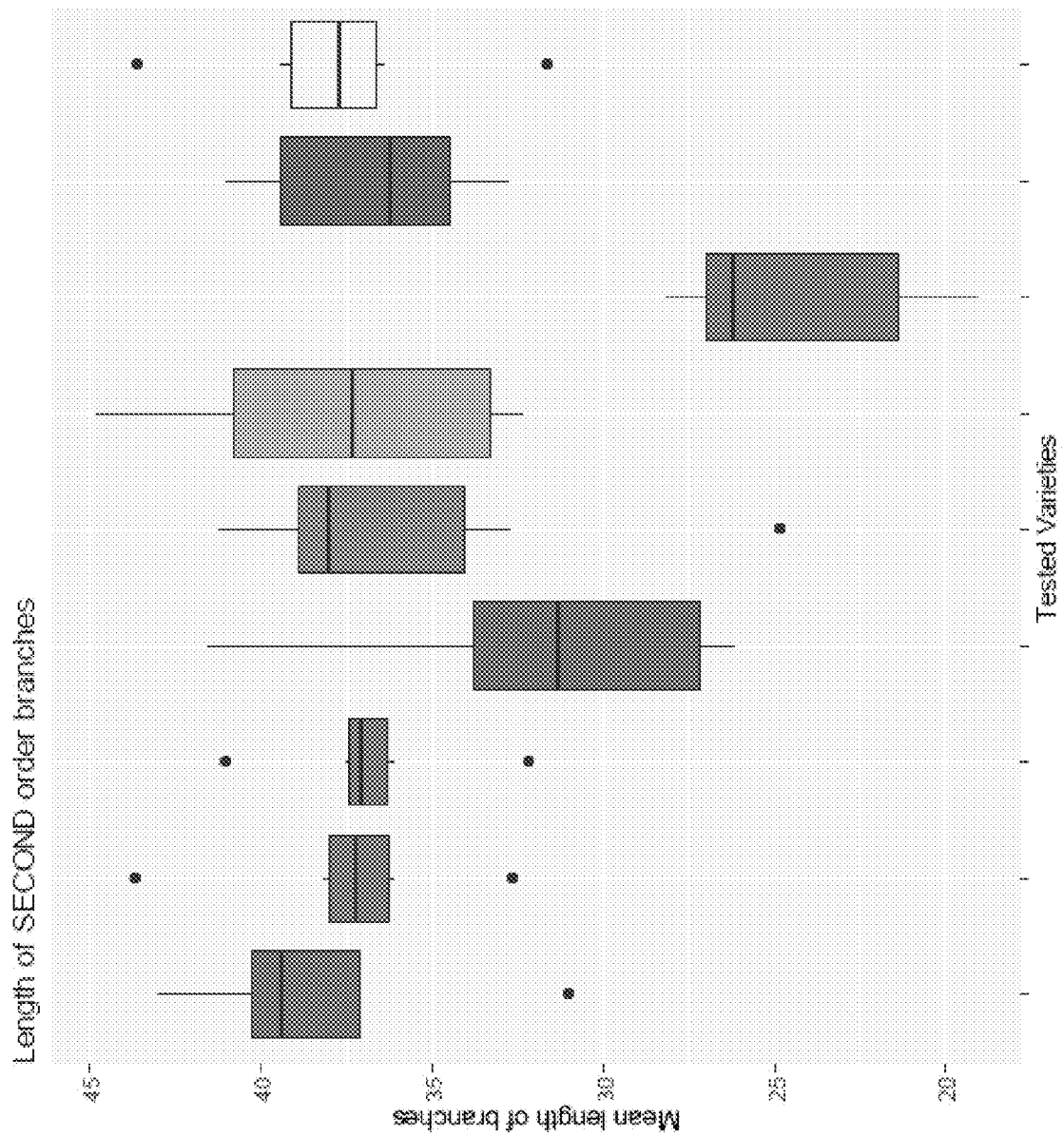

The length of second order branches of 'Green Leaf White 1605-01T1' compared to other *Begonia* varieties was quantified, as shown in FIG. 12C and Table 4. A LSD test placed 'Green Leaf White 1605-01T1' as a member of the group with the longest second order branches, and not in the same group as the variety Tophat™ White.

TABLE 4

| Begonia variety | Length of second order branches | LSD Test Group |
| --- | --- | --- |
| BIG ® Red Bronze Leaf | 38.17267 | a |
| Viking XL Red Green Leaf | 37.76452 | a |
| Megawatt ™ Red Green Leaf | 37.62607 | a |
| BIG ® Deluxxe Red Bronze Leaf | 37.50885 | a |
| BIG ® Deluxxe Red Green Leaf | 36.83863 | a |
| Viking Red Green Leaf | 36.76598 | a |
| 'Green Leaf White 1605-01T1' | 35.67140 | a |
| BIG ® Red Green Leaf | 31.79624 | ab |
| Tophat ™ White | 24.43056 | b |

Figure 12D:
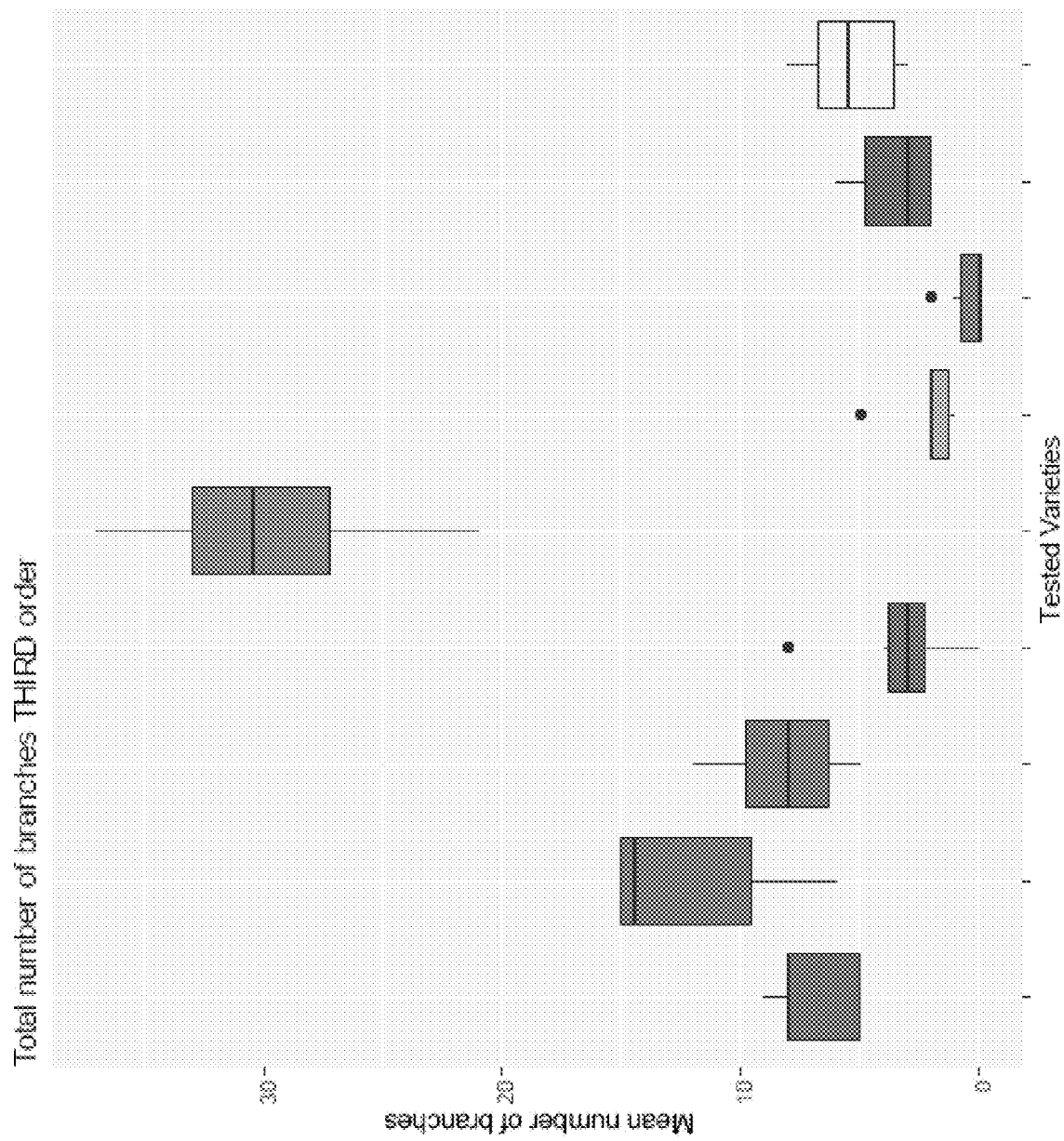

The number of third order branches of 'Green Leaf White 1605-01T1' compared to other *Begonia* varieties was quantified, as shown in FIG. 12D and Table 5. 'Green Leaf White 1605-01T1' was placed in a distinct group by a LSD test, meaning that 'Green Leaf White 1605-01T1' had significantly more third order branches than any other tested *Begonia*. In addition, a one sample t-test to compare the number of third order branches of 'Green Leaf White 1605-01T1' to all other tested varieties showed that the mean total number of third order branches of 'Green Leaf White 1605-01T1' was at least four times that of the other tested *Begonia* varieties (p-value=0.006046).

TABLE 5

| Begonia variety | Number of third order branches | Least Significant Difference Test Group |
| --- | --- | --- |
| 'Green Leaf White 1605-01T1' | 29.833333 | a |
| BIG ® Deluxxe Red Bronze Leaf | 12.166667 | b |
| BIG ® Deluxxe Red Green Leaf | 8.166667 | bc |
| BIG ® Red Bronze Leaf | 7.000000 | bcd |
| Viking XL Red Green Leaf | 5.333333 | cde |
| Viking Red Green Leaf | 3.500000 | cde |
| BIG ® Red Green Leaf | 3.333333 | cde |
| Megawatt ™ Red Green Leaf | 2.166667 | de |
| Tophat ™White | 0.500000 | e |

Figure 12E:
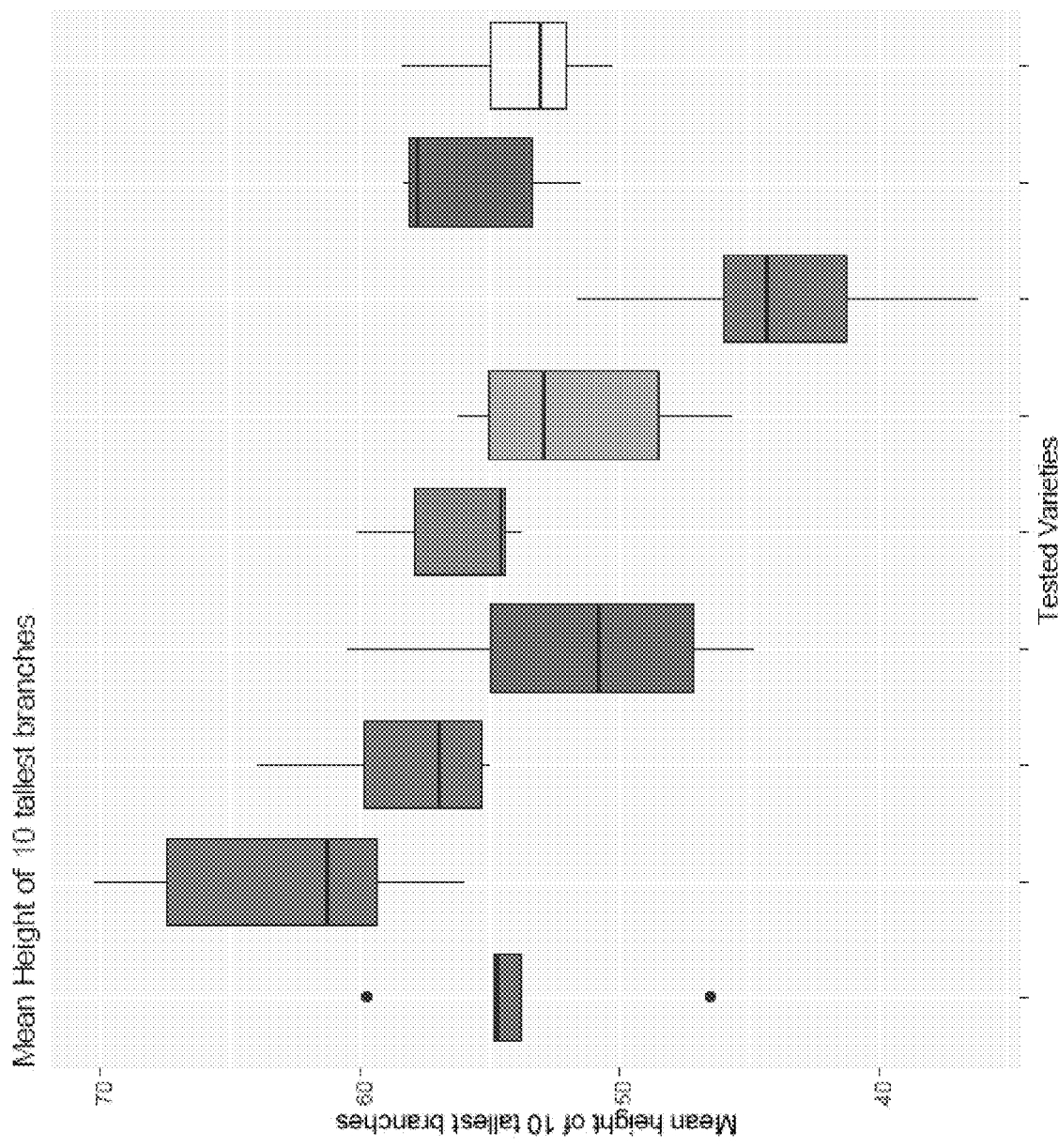

The mean height of the ten tallest plants of 'Green Leaf White 1605-01T1' compared to other *Begonia* varieties was quantified, as shown in FIG. 12E and Table 6. The mean height of the 10 tallest primary branches (first order) was used as proxy for plant height. According to a LSD test, 'Green Leaf White 1605-01T1' was placed in a group with BIG® Deluxxe Red Bronze Leaf and BIG® Deluxxe Red Green Leaf. Therefore, 'Green Leaf White 1605-01T1' reached at least the same height as the other tested *Begonia* varieties.

TABLE 6

| Begonia variety | Mean height of 10 tallest branches | Least Significant Difference Test Group |
| --- | --- | --- |
| BIG ® Deluxxe Red Bronze Leaf | 62.83333 | a |
| BIG ® Deluxxe Red Green Leaf | 58.08667 | ab |
| 'Green Leaf White 1605-01T1' | 56.06667 | ab |
| Viking Red Green Leaf | 55.93333 | ab |
| BIG ® Red Bronze Leaf | 53.95556 | b |
| Viking XL Red Green Leaf | 53.70000 | b |
| Megawatt ™ Red Green Leaf | 51.75000 | bc |
| BIG ®Red Green Leaf | 51.54167 | bc |
| Tophat ™White | 43.88333 | c |

Further distinguishing features are apparent from the comparison of 'Green Leaf White 1605-01T1' with the varieties Tophat™ White and BIG® Green Leaf Red depicted in FIGS. 4A-4C, 5A-5H, 6A-6B, 7A-7D, 8A-8C, 9A-9F, 10A-10H, and 11A-11P.

FURTHER EMBODIMENTS

*Begonia* is an important and valuable flowering plant. Thus, a continuing goal of *Begonia* plant breeders is to develop stable, attractive hybrid begonias that are agronomically sound. To accomplish this goal, the *Begonia* breeder must select and develop *Begonia* plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of *Begonia* plant breeding is to develop new, unique, and superior hybrid begonias. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same *Begonia* traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior hybrid begonias.

The development of commercial hybrid begonias requires the development of *Begonia* varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into *Begonia* varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.,* 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable Umbelliferae," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed *Begonia* plants using transformation methods as described below to incorporate transgenes into the genetic material of the *Begonia* plant(s).

Gene Conversion

When the term "*Begonia* plant" is used in the context of the present disclosure, this also includes any gene conversions of that variety. The term "gene converted plant" as used herein refers to those *Begonia* plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental *Begonia* plant which contributes the gene for the desired characteristic is termed the "nonrecurrent" or "donor parent." This terminology refers to the fact that the nonrecurrent parent is used one time in the backcross protocol and therefore does not recur. The parental *Begonia* plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a *Begonia* plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance or tolerance, resistance or tolerance for bacterial, fungal, or viral disease, insect resistance or tolerance, stress tolerance and/or resistance, industrial usage, yield stability, yield enhancement, physical appearance, drydown, standability, prolificacy, sex determination, improved agronomic quality, improved flower color, improved flower quality and/or quantity, modified phytic acid metabolism, modified protein metabolism, improved plant color, improved plant size, improved habit size and shape, improved leaf size and shape, improved seasonal performance, improved branching, improved flowering, and the like. These genes are generally inherited through the nucleus. Several of these gene traits are described in U.S. Pat. Nos. 5,777,196, 5,948,957, and 5,969,212, the disclosures of which are specifically hereby incorporated by reference.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes." Over the last fifteen to twenty years several methods for producing transgenic plants have been developed, and the present invention, in particular embodiments, also relates to transformed versions of the claimed hybrid.

Tissue Culture

Further reproduction of the variety can occur by tissue culture and regeneration. Tissue culture of various tissues of *Begonia* and regeneration of plants therefrom is well known and widely published. For example, reference may be had to Teng, et al., *HortScience*. 1992, 27: 9, 1030-1032 Teng, et al., *HortScience*. 1993, 28: 6, 669-1671, Zhang, et al., *Journal of Genetics and Breeding*. 1992, 46: 3, 287-290, Webb, et al., *Plant Cell Tissue and Organ Culture*. 1994, 38: 1, 77-79, Curtis, et al., *Journal of Experimental Botany*. 1994, 45: 279, 1441-1449, Nagata, et al., *Journal for the American Society for Horticultural Science*. 2000, 125: 6, 669-672, and Ibrahim, et al., *Plant Cell, Tissue and Organ Culture*. (1992), 28(2): 139-145. It is clear from the literature that the state of the art is such that these methods of obtaining plants are routinely used and have a very high rate of success. Thus, another aspect of this invention is to provide cells which upon growth and differentiation produce *Begonia* plants having the physiological and morphological characteristics of the *Begonia* hybrid 'Green Leaf White 1605-01T1'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, ovules, embryos, roots, root tips, anthers, pistils, stems, flowers, seeds, petioles, fruit, cells, cotyledon, hypocotyl, meristematic cells, portions thereof, and the like. Means for preparing and maintaining plant tissue culture are well known in the art. By way of example, a tissue culture including organs has been used to produce regenerated plants. U.S. Pat. Nos. 5,959,185; 5,973,234 and 5,977,445 describe certain techniques, the disclosures of which are incorporated herein by reference.

As it is well known in the art, tissue culture of *Begonia* can be used for the in vitro regeneration of *Begonia* plants.

Tissues cultures of various tissues of *Begonia* and regeneration of plants therefrom are well known and published. By way of example, tissue cultures, some comprising organs to be used to produce regenerated plants, have been described in Burza, et al., *Plant Breeding*. 1995, 114: 4, 341-345, Pellinen, *Angewandte Botanik*. 1997, 71: 3/4, 116-118, Kuijpers, et al., *Plant Cell Tissue and Organ Culture*. 1996, 46: 1, 81-83, Colijn-Hooymans, et al., *Plant Cell Tissue and Organ Culture*. 1994, 39: 3, 211-217, Lou, et al., *HortScience*. 1994, 29: 8, 906-909, Tabei, et al., *Breeding Science*. 1994, 44: 1, 47-51, Sarmanto, et al., *Plant Cell Tissue and Organ Culture* 31:3 185-193 (1992), Cade, et al., *Journal of the American Society for Horticultural Science* 115:4 691-696 (1990), Chee, et al., *HortScience* 25:7, 792-793 (1990), Kim, et al., *HortScience* 24:4 702 (1989), Punja, et al., *Plant Cell Report* 9:2 61-64 (1990). *Begonia* plants could be regenerated by somatic embryogenesis. It is clear from the literature that the state of the art is such that these methods of obtaining plants are "conventional" in the sense that they are routinely used and have a very high rate of success. Thus, another aspect of this invention is to provide cells which upon growth and differentiation produce *Begonia* plants having the physiological and morphological characteristics of hybrid *Begonia* 'Green Leaf White 1605-01T1'.

Additional Breeding Methods

The present disclosure is also directed to methods for using *Begonia* hybrid 'Green Leaf White 1605-01T1' for transformation where exogenous genes are introduced and expressed by the cultivar of the invention. Genetic variants created either through traditional breeding methods using *Begonia* hybrid 'Green Leaf White 1605-01T1' or through transformation of *Begonia* hybrid 'Green Leaf White 1605-01T1' by any of a number of protocols known to those of skill in the art are intended to be within the scope of this invention.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes *Begonia* hybrid 'Green Leaf White 1605-01T1' progeny *Begonia* plants comprising a combination of at least two hybrid 'Green Leaf White 1605-01T1' traits selected from the group consisting of those listed above or the hybrid 'Green Leaf White 1605-01T1' combination of traits listed in the Summary of the Invention, so that said progeny *Begonia* plant is not significantly different for said traits than *Begonia* hybrid 'Green Leaf White 1605-01T1' as determined at the 5% significance level when grown in the same environmental conditions. Using techniques described herein, molecular markers may be used to identify said progeny plant as a *Begonia* hybrid 'Green Leaf White 1605-01T1' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

As used herein, the term "plant" includes plant cells, plant protoplasts, plant cell tissue cultures from which *Begonia* plants can be regenerated, plant calli, plant clumps and plant cells that are intact in plants or parts of plants, such as fruit, leaves, pollen, embryos, cotyledons, hypocotyl, roots, root tips, anthers, pistils, flowers, seeds, stems, cells, portions thereof, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid *Begonia* 'Green Leaf White 1605-01T1' is maintained by Ernst Benary Samenzucht GmbH, having an address at Friedrich-Benary-Weg 1, 34346 Hann. Münden, Germany. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 2,500 seeds of the same variety made according to the Budapest Treaty in the American Type Culture Collection, (ATCC), ATCC Patent Depository, 10801 University Boulevard, Manassas, Va., 20110, USA.

At least 625 seeds of hybrid *Begonia* 'Green Leaf White 1605-01T1' were deposited on DATE according to the Budapest Treaty in the American Type Culture Collection (ATCC), ATCC Patent Depository, 10801 University Boulevard, Manassas, Va., 20110, USA. The deposit has been assigned ATCC number PTA-126675. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the ATCC depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:

1. Hybrid *Begonia* seed designated as 'Green Leaf White 1605-01T1', representative sample of seed having been deposited under ATCC Accession Number PTA-126675.

2. A *Begonia* plant produced by growing the seed of claim 1.

3. A plant part from the plant of claim 2.

4. The plant part of claim 3, wherein said part is a flower, a leaf, a stem, a cell, or a portion thereof.

5. The plant part of claim 4, wherein said part is a flower.

6. A *Begonia* plant having all the physiological and morphological characteristics of the *Begonia* plant of claim 2.

7. A plant part from the plant of claim 6.

8. The plant part of claim 7, wherein said part is a flower, a leaf, a stem, a cell, or a portion thereof.

9. The plant part of claim 8, wherein said part is a flower.

10. Pollen or an ovule of the plant of claim 2.

11. A protoplast produced from the plant of claim 2.

12. A tissue culture produced from protoplasts or cells from the plant of claim 2, wherein said cells or protoplasts are produced from a plant part selected from the group consisting of leaf, anther, pistil, stem, petiole, root, root tip, fruit, flower, cotyledon, hypocotyl, and meristematic cell.

13. A *Begonia* plant regenerated from the tissue culture of claim 12, wherein the plant has all of the morphological and physiological characteristics of a *Begonia* plant produced by growing hybrid *Begonia* seed designated as 'Green Leaf White 1605-01T1', representative sample of seed having been deposited under ATCC Accession Number PTA-126675.

* * * * *